(12) United States Patent
Amini et al.

(10) Patent No.: US 11,926,876 B2
(45) Date of Patent: Mar. 12, 2024

(54) CUSTOMIZED SKIN CARE PRODUCTS AND PERSONAL CARE PRODUCTS BASED ON THE ANALYSIS OF SKIN FLORA

(71) Applicant: PRODERMIQ, INC., San Diego, CA (US)

(72) Inventors: Sasan Amini, San Diego, CA (US); Dana Hosseini, San Diego, CA (US)

(73) Assignee: PRODERMIQ, INC., San Diego, CA (US)

( * ) Notice: Subject to any disclaimer, the term of this patent is extended or adjusted under 35 U.S.C. 154(b) by 1112 days.

(21) Appl. No.: 16/492,079

(22) PCT Filed: Mar. 9, 2018

(86) PCT No.: PCT/US2018/021862
§ 371 (c)(1),
(2) Date: Dec. 19, 2019

(87) PCT Pub. No.: WO2018/165621
PCT Pub. Date: Sep. 13, 2018

(65) Prior Publication Data
US 2020/0102600 A1     Apr. 2, 2020

Related U.S. Application Data

(60) Provisional application No. 62/469,655, filed on Mar. 10, 2017.

(51) Int. Cl.
| | | |
|---|---|---|
| *C12Q 1/689* | (2018.01) | |
| *G16B 5/00* | (2019.01) | |
| *G16B 30/00* | (2019.01) | |
| *G16B 40/00* | (2019.01) | |

(52) U.S. Cl.
CPC ............... *C12Q 1/689* (2013.01); *G16B 5/00* (2019.02); *G16B 30/00* (2019.02); *G16B 40/00* (2019.02)

(58) Field of Classification Search
CPC .................................. C12Q 1/68; C12Q 1/689
See application file for complete search history.

(56) References Cited

U.S. PATENT DOCUMENTS

| | | |
|---|---|---|
| 6,203,987 B1 | 3/2001 | Friend et al. |
| 7,827,042 B2 | 11/2010 | Jung et al. |
| 7,919,250 B2 | 4/2011 | Blaser et al. |
| 7,927,787 B2 | 4/2011 | Jung et al. |
| 7,974,856 B2 | 7/2011 | Jung et al. |
| 7,989,165 B2 | 8/2011 | Benson |
| 8,000,981 B2 | 8/2011 | Jung et al. |
| 8,297,028 B2 | 10/2012 | Jung et al. |
| 8,340,944 B2 | 12/2012 | Jung et al. |
| 8,468,029 B2 | 6/2013 | Jung et al. |
| 8,532,938 B2 | 9/2013 | Jung et al. |
| 8,793,141 B2 | 7/2014 | Jung et al. |
| 10,169,541 B2 | 1/2019 | Apte et al. |
| 10,354,756 B2 | 7/2019 | Apte et al. |
| 10,364,473 B2 | 7/2019 | Li et al. |
| 10,366,793 B2 | 7/2019 | Apte et al. |
| 10,381,112 B2 | 8/2019 | Apte et al. |
| 10,381,117 B2 | 8/2019 | Apte et al. |
| 10,395,777 B2 | 8/2019 | Apte et al. |

(Continued)

FOREIGN PATENT DOCUMENTS

| | | |
|---|---|---|
| CN | 105407728 A | 3/2016 |
| CN | 105593372 A | 5/2016 |

(Continued)

OTHER PUBLICATIONS

De Geest et al., Periodontal diseases as a source of halitosis: a review of the evidence and treatment approaches for dentists and dental hygienists. Periodontology 2000 (Abstract Only) (Year: 2016).*
Di Bartolomeo et al., Prebiotics to Fight Disease :Reality or Fiction. Phytotherapy Research 27:157-1473 (Year: 2013).*
Dreno et al., Skin microbiome and acne vulgaris: *Staphylococcus*, a new actor in acne. Experimental Dermatology 26:798-803 (Year: 2016).*
Fredrich et al., Daily Battle against body odor : towards the activity of the axillary microbiota. Trends in Microbiology 21(6) : 305 (Year: 2013).*
German et al., Deep Learning tools for Human Microbiome big data. in Soft Computing Applications, Advances in Intelligent Systems and Computing 633 (SOFA 2016) Ed. V.F. Balas Springer International Publishing (Year: 2016).*

(Continued)

*Primary Examiner* — Ethan C Whisenant
(74) *Attorney, Agent, or Firm* — WILSON SONSINI GOODRICH & ROSATI

(57) ABSTRACT

Embodiments of the present invention relate to a combination of experimental and computational workflows that allow characterization of skin and subcutaneous tissue microbial flora and its associated metabolome, aiming to first evaluate an individual's skin and subcutaneous tissue to determine if any skin condition is as a result of an imbalance or absence of commensal or mutualistic microorganisms or their associated metabolites. In particular, embodiments of the methods and the associated computational platform provided herein relate to conducting a customized or personalized test and obtaining customized or personalized information regarding the skin and subcutaneous tissue flora and its associated metabolome there from. This may be accomplished by simultaneously identifying hundreds of microorganisms or metabolites on an individual's skin and subcutaneous tissue and comparing the resulting profile to a previously compiled healthy profile from our database of skin profiles. An individual's profile provides the basis of a proprietary probiotic skin care product and personal care products that either maintains a health profile or shifts the individual's skin and subcutaneous tissue flora or its associated metabolome close to a healthy profile, at the same time enhancing the synergies between the microbial flora and host's immune system.

9 Claims, 18 Drawing Sheets

(56) References Cited

U.S. PATENT DOCUMENTS

| | | | |
|---|---|---|---|
| 10,410,749 | B2 | 9/2019 | Apte et al. |
| 10,679,725 | B2 * | 6/2020 | Hosseini ............... C12Q 1/689 |
| 11,072,832 | B2 * | 7/2021 | Amini ..................... A61P 17/00 |
| 11,211,143 | B2 * | 12/2021 | Hosseini ............... A61B 34/10 |
| 2007/0202540 | A1 | 8/2007 | Benson |
| 2009/0035329 | A1 | 2/2009 | Blaser et al. |
| 2010/0331641 | A1 | 12/2010 | Bangera et al. |
| 2012/0149584 | A1 | 6/2012 | Olle et al. |
| 2013/0121968 | A1 | 5/2013 | Quay |
| 2015/0213193 | A1 | 7/2015 | Apte et al. |
| 2015/0259728 | A1 * | 9/2015 | Cutliffe ................. C12Q 1/689 |
| | | | 435/7.1 |
| 2016/0122806 | A1 * | 5/2016 | Amini ................... C12Q 1/689 |
| | | | 514/789 |
| 2016/0215326 | A1 | 7/2016 | Martin et al. |
| 2016/0230217 | A1 * | 8/2016 | Apte ..................... G16H 20/10 |
| 2017/0228514 | A1 * | 8/2017 | Apte ..................... G16B 50/30 |
| 2017/0235902 | A1 | 8/2017 | Almonacid et al. |
| 2017/0344719 | A1 | 11/2017 | Apte et al. |
| 2018/0030516 | A1 | 2/2018 | Nawana et al. |
| 2018/0080065 | A1 * | 3/2018 | Jain ..................... C12Q 1/6806 |
| 2018/0137243 | A1 | 5/2018 | Belnap |
| 2019/0050534 | A1 | 2/2019 | Apte et al. |
| 2019/0156919 | A1 * | 5/2019 | Magis ................... G16B 50/00 |
| 2019/0213226 | A1 | 7/2019 | Ludwinski et al. |
| 2019/0237194 | A1 | 8/2019 | Salvi et al. |
| 2019/0290605 | A1 * | 9/2019 | Rasochova ............ A61K 45/06 |
| 2019/0292577 | A1 | 9/2019 | Amini et al. |
| 2019/0314428 | A1 * | 10/2019 | Pätzold .................. A61P 17/08 |
| 2021/0310054 | A1 | 10/2021 | Amini et al. |
| 2022/0142560 | A1 * | 5/2022 | Oddos .................... C12N 1/205 |

FOREIGN PATENT DOCUMENTS

| | | | | |
|---|---|---|---|---|
| JP | 2021519096 | A | | 8/2021 |
| WO | WO-2014205088 | A2 | | 12/2014 |
| WO | WO2016174677 | | * | 3/2016 |
| WO | WO-2016079731 | A2 | * | 5/2016 ............... C12Q 1/04 |
| WO | WO-2016172196 | A1 | | 10/2016 |
| WO | WO-2016174677 | A1 | | 11/2016 |
| WO | WO-2017049103 | A1 | | 3/2017 |
| WO | WO-2017109059 | A1 | | 6/2017 |
| WO | WO-2017189614 | A1 | | 11/2017 |
| WO | WO-2018165621 | A1 | | 9/2018 |
| WO | WO-2019191141 | A1 | | 10/2019 |

OTHER PUBLICATIONS

Grice, EA.. The skin microbiome: potential for novel diagnostic and therapeutic approaches to cutaneous disease. Semin Cutan Med Surg 33(2) :98-103 (Year: 2015).*
Huang et al., Trends in extreme learning machines : A review. Neural Networks 61: 32-48 (Year: 2015).*
Johnson et al., A machine learning approach for using the postmortem skin microbiome to estimate the postmortem interval. PlosOne 11(12) : e0167370 (Year: 2016).*
LeCun et al. Deep Learning. Nature 521:436 (Year: 2015).*
Liu et al. Deep Sequencing of the Oral Microbiome reveals Signatures of Peridontal Disease. PlosOne 7(6) : e37919 (Year: 2012).*
Leyden et al., The Microbiology of the Human Axilla and its relationship to Axillary Odor. J. of Investigative Dermatology 77:413 (Year: 1981).*
Schmidhuber, J. Deep Learning in neural Networks : An Overview. Neural Networks 61 :85-117 (Year: 2015).*
Tangerman et al., Extra-oral Halitosis : an overview . J. of Breth Research 4: 1017003(6 pp) (Year: 2010).*
Australian Patent Application No. 2014281553 Examination Report dated Sep. 11, 2019.
Baehrecke, EH. Autophagic programmed cell death in *Drosophila*. Cell Death Differ. 10(9):940-945 (2003).
Bartel, DP. MicroRNAs: genomics, biogenesis, mechanism, and function. Cell. 116(2): 281-297 (2003).
Brennecke et al., "Bantam encodes a developmentally regulated microRNA that controls cell proliferation and regulates the proapoptotic gene hid in *Drosophila*," Cell, 113: 25-36 (2003).
Brown et al., The Formulation of Bacteriophage in a Semi Solid Preparation for Control of Propionibacteriumacnes Growth. PLoS One. 11(3):e0151184 (2016).
Chen et al. MicroRNAs modulate hematopoietic lineage differentiation. Science 303(5654):83-86 (2004).
Fitz-Gibbon et al., Propionibacterium acnes strain populations in the human skin microbiome associated with acne. J.Invest. Dermatology. 133(9):2152-2160 (2013).
Grice et al.: Topographical and Temporal Diversity of the Human Skin Microbiome; Science; 324(5931):1190-1192 (2009).
Kong, Heidi H. et al. Skinmicrobiome: genomics-based insights into the diversity and role of skin microbes. Trends in Molecular Medicine, 17(6):320-327 (2011).
Lee et al. The C. elegans heterochronic gene lin-4 encodes small RNAs with antisense complementarity to lin-14. Cell 75:843-854 (1993).
Mills et al., Comparing 2.5%, 5%, and 10% benzoyl peroxide on inflammatory acne vulgaris. International Journal of Dermatology. 25(10):664-667 (1986).
PCT/US2019/024144 International Search Report an Written Opinion dated Jun. 24, 2019.
Reinhart et al. The 21-nucleotide let-7 RNA regulates developmental timing in Caenorhabditis elegans. Nature 403(6772):901-906 (2000).
Yi et al. Morphogenesis in skin is governed by discrete sets of differentially expressed microRNAs. Nature Genetics 38(3):356-362 (2006).
Chinese Patent Application No. 2014800386819 Decision of Final Rejection dated Sep. 2, 2021.
Davey et al., Genome-wide genetic marker discovery and genotyping using next-generation sequencing. Nature Reviews 12: 499-510 (2011).
Extended European Search Report dated Aug. 24, 2021 for European Application No. 19777961.4.
Leyden, J. et al., "The Microbiology of the Human Axilla and its Relationship to Axillary Odor", The Journal of Investigative Dermatology, 1981, vol. 77, No. 5, pp. 413-416.
Paliwal et al., Diagnostic Opportunities Based on SkinBiomarkers. Eur J Pharm Sci 50: 546-556 (2013).
PCT/US2018/021862 International Search Report dated May 16, 2018.
Petrosino et al., Metagenomic Pyrosequencing and Microbial Identification. Clinical Chemistry 55(5): 856-866 (2009).
Zhang et al., Modern analytical techniques in metabolomics analysis. Analyst 137: 293 (2012).
May 2, 2022 Restriction Requirement U.S. Appl. No. 16/365,530.
Communication pursuant to Article 94(3) EPC dated Apr. 11, 20220 for European Application No. 19219640.0.
European Application No. 14813865.4 Extended European Search Report dated Feb. 1, 2017.
Extended European Search Report dated Dec. 1, 2020 for European Application No. 18764855.5.
Leyden, J. et al. The microbiology of the Human Axilla and Its Relationship o Axillary Odor. The Journal of Investigative Dermatology. 77(5):413-416 (Nov. 1981).
Morgan, X.C., et al., "Chapter 12: Human Microbiome Analysis", PLOS Computational Biology, 2012, vol. 8, No. 12, e1002808, pp. 1-14.
PCT/US2014/042961 International Preliminary Report on Patentability dated Dec. 22, 2015.
PCT/US2014/042961 International Search Report and Written Opinion dated Mar. 10, 2015.
PCT/US2018/021862 International Preliminary Report on Patentability dated Sep. 10, 2019.
U.S. Appl. No. 14/899,048 Final Office Action dated May 12, 2017.
U.S. Appl. No. 14/899,048 Non-Final Office Action dated Apr. 24, 2018.
U.S. Appl. No. 14/899,048 Non-Final Office Action dated Oct. 17, 2016.

(56) References Cited

OTHER PUBLICATIONS

European Application No. 18764855.5 Communication pursuant to Article 94(3) EPC dated Nov. 30, 2021.
Baylor College of Medicine. The Human Microbiome Project. Available at: https://www.bcm.edu/departments/molecular-virology-and-microbiology/research/the-human-microbiome-project (2012).
Beebe, Is Metabolomics the Rosetta Stone for Understanding the Microbiome? (2017).
Clear Skin Probiotic Cleaner 250mL, Eminence Organic Skin Care. (2013).
European Application No. 19219640 Search Report dated Sep. 1, 2020.
Grice et al. The skin mirobiome. Nat Rev Microbiol 9(4):244-253 (2011).
Kong et al. Temporal shifts in the skin microbiome associated with disease flares and treatment in children with atopic dermatitis. Genome Res 22(5):850-859 (2012).
Larsen et al., Metabolome of human gut microbiome is predictive of host dysbiosis. Gigascience 4(1) 16 pages (2015).
PCT/US2019/024144 International Preliminary Report on Patentability dated Sep. 29, 2020.
Peterson, The NIH Human Microbiome Project. Genome Research 19: 2317-2323 (2009).
Pray et al., Study of Human Mirobiome. The Human Microbiome, Diet, and Health: Workshop. The National Academies Press (US), Washington, DC. vol. 2, ISBN 978-0-309-26585-0: pp. 33-54 (2013).
Shaffer et al., Microbiome and metabolome data integration provides insight into health and disease. Transl Res 189: 51-64 (2017).
Turnbaugh et al., The Human Microbiome Project. Nature 449: 804-810 (2007).
U.S. Appl. No. 14/899,048 Non-Final Office Action dated Dec. 24, 2020.
U.S. Appl. No. 14/899,048 Final Office Action dated Jan. 3, 2020.
Yang et al., Integrating '-omics' and natural product discovery platforms to investigate metabolic exchange in microbiomes. Current Opinion in Chemical Biology 15(1): 79-87 (2011).
Mar. 15, 2023 Final Office Action U.S. Appl. No. 16/365,530.
Aug. 15, 2022 Non-Final Office Action U.S. Appl. No. 16/365,530.
Chinese Patent Application No. 201880030985.9 Office Action dated Jan. 13, 2023.
Communication pursuant to Article 94(3) EPC dated May 3, 2023 for European Application No. 19219640.0.
Japanese Patent Application No. 2020-552270 Office Action dated Mar. 2, 2023.
Korean Patent Application No. 10-2019-7029763 Office Action dated Jun. 19, 2023.

\* cited by examiner

CUSTOMIZED SKIN CARE PRODUCTS AND PERSONAL CARE PRODUCTS BASED ON THE ANALYSIS OF SKIN FLORA

CROSS REFERENCE

This application claims the benefit of priority from U.S. Provisional Patent Application No. 62/469,655, filed Mar. 10, 2017, which is incorporated herein by reference in its entirety.

BACKGROUND

About 100 trillion microorganisms live in and on the human body vastly outnumbering the body's approximately 10 trillion human cells. These normally harmless viruses, bacteria and fungi are referred to as commensal or mutualistic organisms.

SUMMARY

Commensal and mutualistic organisms help keep our bodies healthy in many ways: they help us to digest foods and acquire nutrients such as vitamins B and K, encourage the immune system to develop and prevent the colonization of, for example, bacterial pathogens that cause disease by competing with them. Together all of the microorganisms living in and on the body of an individual—commensal, mutualistic and pathogenic—are referred to as the microbiome. The metabolic processes and/or the products of the metabolic processes of the organisms that comprise the microbiome of the body of an individual are referred to as a metabolome. The equilibrium of organisms within the microbiome and the metabolome associated with these organisms that comprise the microbiome are closely linked to an individual's health status and vice-versa.

Described herein are systems and methods for generating customized skin care and personal care products for human and animal use and, more particularly, but not by way of limitation, to the development of personal care products that are based on the initial evaluation of the flora and/or metabolic activity of the flora inhabiting the skin and subcutaneous tissue.

Described herein are systems and methods for analyzing the skin and subcutaneous tissue flora, e.g., the microbiome, and its associated metabolome, comparing the resulting profile of the skin and subcutaneous tissue flora and metabolome to a healthy profile, represented as a quantity and diversity of flora that falls within a range determined from a set of healthy skin types and/or unhealthy skin types, and then customizing skin care and personal care products that will augment the flora residing on a test subject's skin and subcutaneous tissue and its associated metabolome or replicate a healthy flora profile on to that of a test subject.

Next generation sequencing (NGS) has created an opportunity to quickly and accurately identify and profile the microbiome inhabiting the skin and subcutaneous tissue, which then creates an opportunity for the creation of customized or personalized skin care and personal care products that either maintain a healthy microbiome or shift a profile towards a healthy equilibrium or profile by blending a mixture of commensal and/or mutualistic organisms specifically created to establish a healthy profile. The optimal flora also interacts with the host immune system in a synergistic way further propagating its health benefits. The associated metabolome of individuals can also be profiled either by a mass-spectrometry based system or using genomics-based metabolome modeling and flux-balance analysis and used to make a healthy metabolome profile. Deficiencies in any of the beneficial metabolites can be supplemented as well.

Traditional treatments of certain dermatological conditions comprise antibiotics that drastically impact the microbiome including the commensal and mutualistic bacteria. Other traditional treatments of certain dermatological conditions comprise anti-inflammatory agents such as steroids that have local and systemic effects on immune response. Both of these traditional treatments, antibiotic and steroid based therapies, may fail to address the underlying cause of a skin condition if it is due to an imbalance or absence of commensal or mutualistic microorganisms, overabundance of opportunistic or pathogenic bacteria, or deficiencies of essential or beneficial metabolites.

Described herein is a method of characterizing a microbiome of skin or subcutaneous tissue of a subject. The method includes: a) obtaining a sample comprising a plurality of microorganisms from the skin or subcutaneous tissue of the subject; and b) analyzing and classifying the plurality of microorganisms to characterize the microbiome of the subject, thereby characterizing the microbiome of the subject. In some embodiments, the method further includes comparing the microbiome of the subject to a reference microbiome or generating a microbiome profile of the subject, or identifying a disease or disorder which the subject has, or is at risk of developing, or providing a personalized treatment regime to the subject. In various embodiments, the reference microbiome is classified as having a healthy profile and a similarity between the microbiome of the subject and the reference microbiome identifies the microbiome of the subject as having a healthy profile. Alternatively, the reference microbiome is classified as having, or at risk of having a disease or disorder and a similarity between the microbiome of the subject and the reference microbiome identifies the microbiome of the subject as having as having, or at risk of having the disease or disorder.

In another aspect, the invention provides a method of characterizing microbiomes of skin or subcutaneous tissue of a plurality of subjects. The method includes: a) obtaining a plurality of samples from the skin or subcutaneous tissue of the plurality of subjects, each sample comprising a plurality of microorganisms; and b) analyzing and classifying the plurality of microorganisms of each sample of the plurality of samples to identify a microbiome of each of the plurality of samples, thereby generating an analysis result comprising a characterization of the microbiomes of the plurality of subjects. In some embodiments, the method further includes clustering the analysis result to identify individual cohorts of the plurality of samples. In some embodiments, the each individual cohort exhibits a particular phenotype or profile. In some embodiments, each individual cohort includes samples having similar microbiomes, samples from subjects having a common skin disease or disorder, or samples from subjects having a similar metabolite profile.

In yet another aspect, the present invention provides a method of diagnosing a disease or disorder in a subject. The method includes a) obtaining a sample comprising a plurality of microorganisms from the skin or subcutaneous tissue of the subject; b) analyzing and classifying the plurality of microorganisms to identify a microbiome of the subject; and c) comparing the microbiome of the subject to a reference microbiome representative of a microbiome of a subject having or at risk of the disease or disorder, wherein a similarity between the microbiome of the subject and the reference microbiome is indicative of the subject being at risk of, or having the disease or disorder, thereby diagnosing a disease or disorder in the subject. In some embodiments the method further includes providing a personalized treatment regime to the subject. In some embodiments the method further includes formulating and administering a customized therapeutic formulation to the subject.

In another aspect, the invention provides a method of formulating a customized therapeutic formulation for a subject having, or at risk of a disease or disorder. The method includes: a) obtaining a sample comprising a plurality of microorganisms from the skin or subcutaneous tissue of the subject; b) analyzing and classifying the plurality of microorganisms to identify a microbiome of the subject; c) comparing the microbiome of the subject to a reference microbiome representative of a microbiome of a subject having or at risk of the disease or disorder, wherein a similarity between the microbiome of the subject and the reference microbiome is indicative of the subject being at risk of the disease or disorder, or having the disease or disorder; and d) formulating a customized therapeutic formulation based on the comparison of the microbiome of the subject to a reference microbiome representative of a microbiome of a subject having or at risk of the disease or disorder, thereby formulating a customized therapeutic formulation. In another aspect, the subject is provided with a therapeutic formulation formulated via the method.

Described herein is a method of characterizing a microbiome of a tissue of a subject to assess body odor. The method includes: a) obtaining a sample comprising a plurality of microorganisms from the subject; b) analyzing and classifying the plurality of microorganisms to characterize the microbiome of the subject; c) classifying the subject as having low body odor or high body odor; and d) optionally administering a composition, such as a therapeutic formulation to the subject, thereby characterizing the microbiome of the subject. In embodiments, the bacterium is of the genus *Propionibacteria, Staphylococci* or *Corynebacteria*. In one embodiment, classifying includes determining the proportion of different species of a bacterial strain, such as different species of *Propionibacterium acnes*.

Described herein is a method of assessing and treating body odor of a subject. The method includes: a) obtaining a sample comprising bacteria from the subject; b) analyzing and classifying the bacteria to characterize a microbiome of the subject, wherein analyzing and classifying comprises determining the abundance of different species of *Propionibacterium acnes*; c) providing an assessment of body odor of the subject based on the abundance of different species of *Propionibacterium* acne; and d) optionally administering a composition, such as a therapeutic formulation to the subject, thereby assessing and treating body odor of the subject.

Described herein is a method for characterizing an individual who provides a microbiome, comprising: generating a sequence profile comprising a nucleotide sequence associated with said microbiome; generating a metabolome profile selected from the group consisting of a cellular growth rate associated with said microbiome, a nutrient uptake rate associated with said microbiome, and a byproduct secretion rate associated with said microbiome; comparing said sequence profile and said metabolome profile to a reference profile thereby generating a comparison result; and generating a characterization of said individual based on said comparison result. In some embodiments, said sample comprises skin or hair. In some embodiments, plurality of nucleotide sequences are generated using whole genome sequencing. In some embodiments, said plurality of nucleotide sequences are generated using next generation sequencing. In some embodiments, said plurality of nucleotide sequences are generated using Sanger-sequencing. In some embodiments, said plurality of nucleotide sequences are generated using 16S rDNA sequencing. In some embodiments, said plurality of nucleotide sequences are generated using 16S rRNA sequencing. In some embodiments, one or more of said plurality micro-organisms comprises a bacterium from genus *Propionibacteria, Staphylococci*, or *Corynebacteria*. In some embodiments, said metabolic profile is generated using mass-spectrometry. In some embodiments, said one or more reference profiles are generated by a machine learning algorithm trained with microbiome and metabolome data from individuals who do not have a disorder associated with the tissue sample. In some embodiments, said comparison result is generated by a machine learning algorithm trained with microbiome and metabolome data from both individuals who have and individuals who do not have a disorder associated with the tissue sample. In some embodiments, said disorder comprises acne vulgaris. In some embodiments, said disorder comprises body odor. In some embodiments, said characterization of said tissue sample comprises a determination of a presence of a disorder and a relative degree of presence of said disorder within said tissue sample. In some embodiments, one or more of said comparison result, said sequence profile and said metabolome profile is used to determine a custom treatment modality. In some embodiments, said custom treatment modality comprises one or more agents that promote growth of one or more of said plurality of microorganisms.

Described herein is a system for characterizing an individual who provides a microbiome, comprising: a processor; and a non-transitory computer readable storage medium encoded with instructions executable by the processor that cause the processor to: generate a sequence profile comprising a sequence associated with said microbiome; generate a metabolome profile is selected from the group consisting of a cellular growth rate associated with said microbiome, a nutrient uptake rate associated with said microbiome, and a byproduct secretion rate associated with said microbiome; compare said sequence profile and said metabolome profile to one or more reference profiles thereby generating a comparison result; and generate a characterization of said individual based on said comparison result. In some embodiments, said sample comprises skin or hair. In some embodiments, said plurality of nucleotide sequences are generated using whole genome sequencing. In some embodiments, said plurality of nucleotide sequences are generated using next generation sequencing. In some embodiments, said plurality of nucleotide sequences are generated using Sanger-sequencing. In some embodiments, said plurality of nucleotide sequences are generated using 16S rDNA sequencing. In some embodiments, said plurality of nucleotide sequences are generated using 16S rRNA sequencing. In some embodiments, one or more of said plurality micro-organisms comprises a bacterium from genus *Propionibacteria, Staphylococci*, or *Corynebacteria*. In some embodiments, said metabolic profile is generated using mass-spectrometry. In some embodiments, said one or more reference profiles are generated by a machine learning algorithm trained with microbiome and metabolome data from individuals who do not have a disorder associated with the tissue sample. In some embodiments, said comparison result is generated by a machine learning algorithm trained with microbiome and metabolome data from both individuals who have and individuals who do not have a disorder associated with the tissue sample. In some embodiments, said disorder comprises acne vulgaris. In some embodiments, said disorder comprises body odor. In some embodiments, said characterization of said tissue sample comprises a determination of a presence of a disorder and a relative degree of presence of said disorder within said tissue sample. In some embodiments, one or more of said comparison result, said sequence profile and said metabolome profile is used to determine a custom treatment modality. In some embodiments, said custom treatment modality comprises one or more agents that promote growth of one or more of said plurality of micro-organisms.

DETAILED DESCRIPTION

Figure 1:
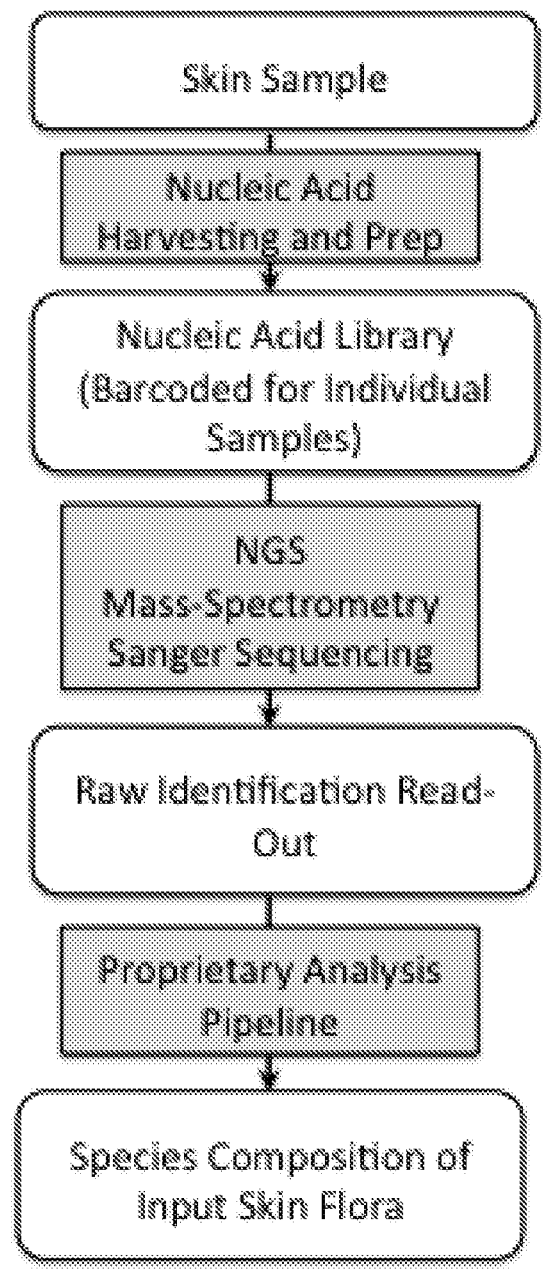
FIG. 1 shows an exemplary experimental and analysis pipeline for profiling skin and subcutaneous tissue flora.

The term "individual" as used herein refers to any human or animal.

Examples of organisms that comprise a microbiome include both prokaryotes and eukaryotes that may colonize (i.e., live and multiply on human skin) or temporarily inhabit human skin in vitro, ex vivo and/or in vivo. Exemplary skin commensal microorganisms include, but are not limited to, Alphaproteobacteria, Betaproteobacteria, Gammaproteobacteria, *Propionibacteria, Corynebacteria*, Actinobacteria, Clostridiales, Lactobacillales, *Staphylococcus, Bacillus, Micrococcus, Streptococcus*, Bacteroidales, Flavobacteriales, *Enterococcus, Pseudomonas, Malassezia, Maydida*, Debaroyomyces, and *Cryptococcus.*

Systems and Methods for Characterizing Microbiome and/or Metabolome Data

Described herein are systems and methods that that characterize a tissue of an individual. In some embodiments of the systems and methods a tissue to be characterized comprises skin. The process of characterization described herein includes an analysis of the microbial flora and/or associated metabolome of a sample taken from, for example, the skin of an individual. In some embodiments, the process of characterization comprises determining if a condition of the tissue (e.g. a disease or disorder) is a result of an imbalance or absence of commensal or mutualistic microorganisms and/or an imbalance or deficiency in the associated metabolome.

Described herein are systems and methods for analyzing samples taken from individuals having certain disorders and diseases in order to characterize the sample, and, in some embodiments, provide a custom therapy to the individuals based on the characterization. More specifically, analysis is performed on the samples to characterize the microbiome and/or metabolome data associated with the sample in terms of: (a) the taxonomy of micro-organisms that comprise the microbiome, (b) the metabolome profile associated with the microbiome, and/or (c) the physical expression of the microbiome and/or metabolome in the individual.

For example, in some embodiments of the systems and methods described herein, a percentage of different bacteria are identified within a sample and an imbalance with respect to the individual's microbiome is detected in the form of overgrowth of a species of micro-organism that is typically in low numbers in the microbiome of normal individuals (or in this individual in a non-diseased state).

For example, in some embodiments of the systems and methods described herein, a metabolome profile is determined in terms of identifying the percentage of metabolites present in a sample taken from an individual and detecting an imbalance in terms of an overproduction of a certain metabolite that is typically in low numbers in normal individuals (or in this individual in a non-diseased state).

For example, in some embodiments of the systems and methods described herein, a physical expression of the microbiome and/or metabolome is identified in the individual by comparing the microbiome and/or metabolome characteristics of the individual to those of normal individuals (or the same individual in a non-diseased state). That is, in some embodiments, a physical expression of the microbiome and/or metabolome of the individual indicates that they have a high amount of body odor based on a comparison of the characteristics of the microbiome and/or metabolome of the individual with the microbiomes and/or metabolomes of others. In this way, an individual is classified. In this specific example, an individual is classified as having a high amount of body odor.

Characterization of a sample taken from an individual, in some embodiments, is based on a comparison of the sample analysis results of one individual to those of one or more health individuals. Healthy individuals provide samples or sample analysis data that is determined to have a healthy microbiome, e.g., free from disease or disorder, or risk thereof and/or is free of a particular disease or disorder. As such, in some embodiments, a reference microbiome is taken from one or more samples of cells obtained from one or more healthy individuals that do not have a skin disorder and/or particular undesirable phenotype. Likewise, a healthy profile comprises a quantity and diversity of flora that falls within a range determined from a set of healthy skin types. The term healthy skin comprises skin that is devoid of a skin condition, disease or disorder, including, but not limited to inflammation, rash, dermatitis, atopic dermatitis, eczema, psoriasis, dandruff, acne, cellulitis, rosacea, warts, seborrheic keratosis, actinic keratosis, tinea *versicolor*, viral exantham, shingles, ringworm, and cancer, such as basal cell carcinoma, squamous cell carcinoma, and melanoma. The systems and methods described herein, in classifying individuals based on sample analysis, also provide the diagnosis of diseases and disorders in certain individuals. Non-limiting examples of diseases and disorders diagnosed by embodiments of the systems and methods described herein include inflammation, rash, dermatitis, atopic dermatitis, eczema, psoriasis, dandruff, acne, cellulitis, rosacea, warts, seborrheic keratosis, actinic keratosis, tinea *versicolor*, viral exantham, shingles, ringworm, and cancer, such as basal cell carcinoma, squamous cell carcinoma, melanoma, carcinoma, and sarcoma.

Samples suitable for use with the systems and methods described herein include a skin or subcutaneous tissue sample obtained by non-invasive techniques such as tape stripping, scraping, swabbing, or more invasive techniques such as biopsy of a subject. It should be understood that samples suitable for use with the systems and methods described herein include any preparation derived from the skin or subcutaneous tissue of an individual. Likewise, samples suitable for use with the systems and methods described herein, in some embodiments, are taken from an area of the skin shown to exhibit a disease or disorder, which is suspected of being the result of a disease or a pathological or physiological state, such as psoriasis or dermatitis, or the surrounding margin or tissue. Likewise, samples taken from a surrounding margin or surrounding tissue refers to tissue of the subject that is adjacent to the skin shown to exhibit a disease or disorder, but otherwise appears to be normal and these types of samples are also suitable for use with the systems and methods described herein. The skin and subcutaneous tissue comprise the outer protective covering of the body, and comprise the epidermis (including the stratum corneum) and the underlying dermis, and is understood to include sweat and sebaceous glands as well as hair follicle structures and nails. Throughout the present application, the adjective "cutaneous" and "subcutaneous" can be used, and should be understood to refer generally to attributes of the skin, as appropriate to the context in which they are used. The epidermis of the human skin comprises several distinct layers of skin tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

A sample of cells obtained using, for example, the non-invasive sample gathering methods described herein is used to isolate nucleic acid molecules or proteins found in, on, or otherwise associated with the sample. More specifically, isolated nucleic acid molecules include DNA and RNA from micro-organisms that comprise a microbiome associated with the sample.

FIG. 1 shows an exemplary method for profiling skin and subcutaneous tissue flora. In a first step, formative regions of the microbial genome from a mixed population, which are collected from a skin or subcutaneous tissue sample, are amplified with universal primer sequences designed to capture maximum diversity of various bacterial species. In a second step, the amplified regions are uniquely indexed to allow multiplex processing of samples from various sources (Nucleic Acid Harvesting and Prep). In a third step, amplified regions from different sources can be combined and sequenced with the Paired End (PE) mode on an NGS platform or alternatively can be analyzed on Sanger-sequencing, mass-spectrometry, quantitative PCR, immunofluorescence, in situ hybridization, or microbial staining based platforms. In a fourth step, raw outputs of the identification platform are assigned to different taxonomy groups. A similar workflow would be utilized for mapping metabolites associated with any given sample.

Figure 2:
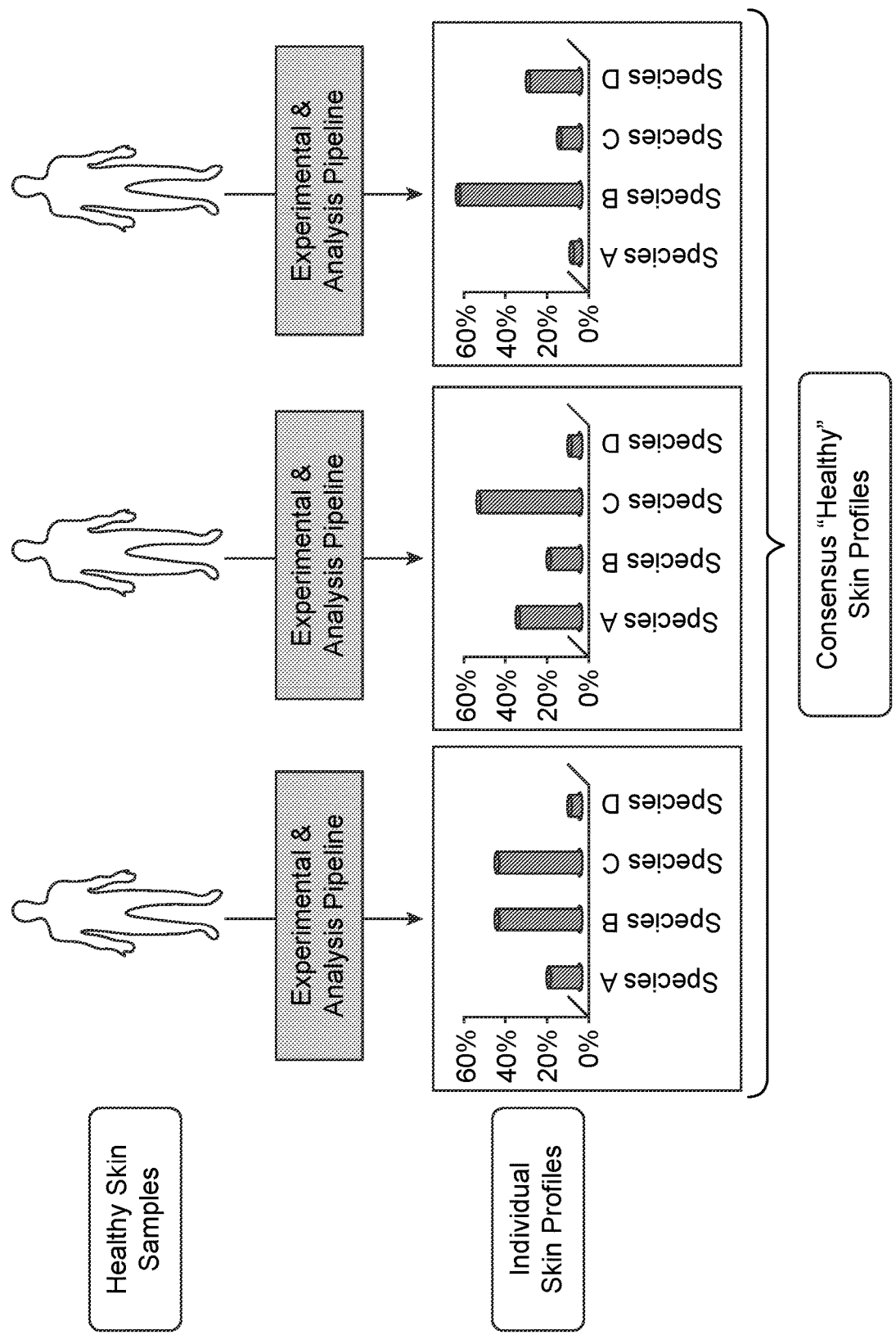
FIG. 2 shows an exemplary schematic of the generation of a healthy consensus profile or a reference profile.

FIG. 2 shows an exemplary schematic of how data is gathered from a healthy cohort of individuals and then processed using the method shown in FIG. 1 to build a consensus profile for the healthy population, capturing the constituent dominant species of flora and/or their associated metabolome. The healthy consensus profile is treated as the reference to compare any affected group, population or individual.

Figure 3:
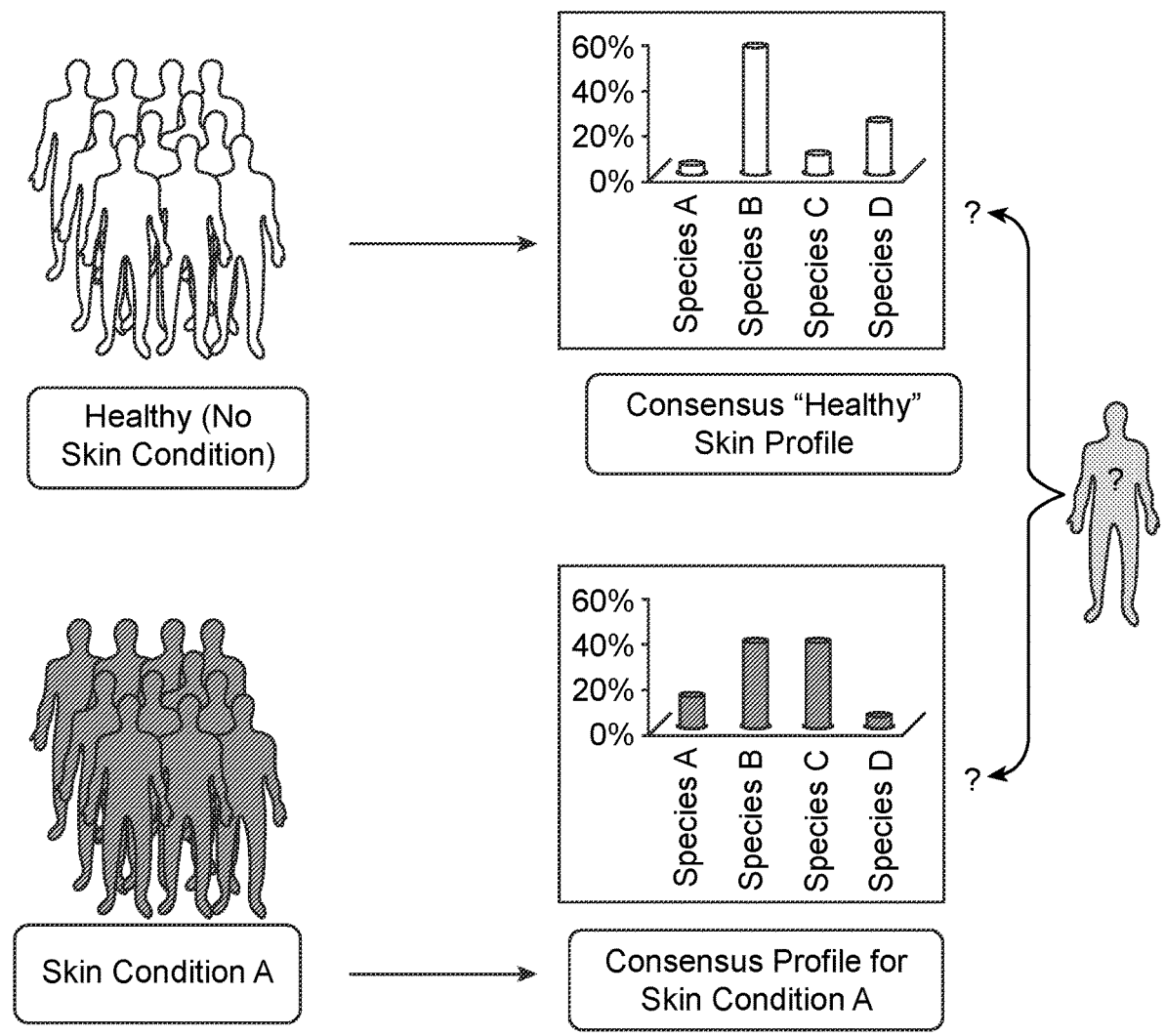
FIG. 3 shows an exemplary schematic of the comparison of one or more samples to one or more reference profiles.

FIG. 3 shows multiple samples from a cohort of individuals with one characteristic skin condition will be collected and their skin flora and its associated metabolome is profiled as described herein. The species meta-data profile is used to identify signature microorganisms or metabolites which are causative of or associated with that skin condition. Contrasted with the healthy profile identified before, any anomaly in skin and subcutaneous tissue flora or metabolome composition of a new client (shown by a question mark in the figure) can be detected even at early stages and can be fixed or remediated with a customized or personalized skin care product which shifts that affected profile towards a healthy equilibrium created by blending a mixture of commensal organism or metabolites specifically expected to establish a healthy profile.

As discussed further herein, Next Generation Sequencing, or "NGS", is a powerful DNA sequencing technology that allows for the rapid and accurate sequencing of cells or organisms, and enables evaluating complex bacterial communities, a good example of which is the microbiome. In some embodiments, identification of inhabitant flora for every individual is conducted on such an NGS platform. Such a platform allows for the rapid and accurate generation of a profile of the microbiome inhabiting the skin of an individual with high enough sensitivity and specificity with a relatively short turn-around time and scalable throughput.

Alternatively, a Sanger-sequencing, mass-spectrometry, quantitative PCR, immunofluorescence, in situ hybridization, or microbial staining based platform can be used to characterize individual profiles. Similarly, the microbiome or metabolome can be profiled either by a mass-spectrometry based system or using genomics-based metabolome modeling and flux-balance analysis. All the above-mentioned identification methods can be implemented on samples directly collected from individuals without any proliferation step. This way, minimal bias is introduced toward identification of a mixture of culturable and unculturable microorganisms or their associated metabolome.

By leveraging the high throughput capabilities of NGS or other microbial identification methods like mass spectrometry or Sanger sequencing, microorganisms on an individual's subcutaneous tissue and their associated microbiome and metabolome will simultaneously be identified and the resulting profile may be compared to a healthy profile from a database of skin and subcutaneous tissue profiles. Independent of which platform is exploited for profiling, the abovementioned platform may be offered as a test to any client and the output may be used to identify which commensal, pathogenic, or mutualistic microorganisms or their associated metabolite are depleted or overrepresented on the subject's skin and subcutaneous tissue compared to the healthy profile.

Probes suitable for use with the systems and methods described herein comprise nucleic acid molecule that are at least partially single-stranded, and that are at least partially complementary, or at least partially substantially complementary, to a sequence of interest. A probe can be RNA, DNA, or a combination of both RNA and DNA. Suitable probes also comprise nucleic acid molecules comprising nucleic acids in which the backbone sugars other than ribose or deoxyribose. Suitable probes also comprise nucleic acids comprising peptide nucleic acids. A probe in some embodiments comprises nucleolytic-activity resistant linkages or detectable labels, and can be operably linked to other moieties, for example a peptide.

Hybridization reactions can be sensitive and selective so that a particular sequence of interest can be identified even in samples in which it is present at low concentrations. In an in vitro situation, suitably stringent conditions can be defined by, for example, the concentrations of salt or formamide in the prehybridization and hybridization solutions, or by the hybridization temperature. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 mg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are envisioned as well.

As such the methods and platforms described herein may utilize analysis of a nucleic acid molecule, such as sequencing a nucleic acid molecule. Sequencing methods may include whole genome sequencing, next generation sequencing, Sanger-sequencing, 16S rDNA sequencing and 16S rRNA sequencing. Further, such methods and platforms described herein may utilize mass-spectrometry, quantitative PCR, immunofluorescence, in situ hybridization, a microbial staining based platform, or combination thereof.

In some embodiments, the input to the identification platform can be any nucleic acid, including DNA, RNA, cDNA, miRNA, mtDNA, single or double-stranded. This nucleic acid can be of any length, as short as oligos of about 5 bp to as long as a megabase or even longer. As used herein, the term "nucleic acid molecule" means DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule. For methods that analyze expression of a gene, the nucleic acid isolated from a sample is typically RNA.

Micro-RNAs (miRNA) are small single stranded RNA molecules an average of 22 nucleotides long that are involved in regulating mRNA expression in diverse species including humans (reviewed in Bartel 2004). The first report of miRNA was that of the lin-4 gene, discovered in the worm *C. elegans* (Lee, Feinbaum et al. 1993). Since then hundreds of miRNAs have been discovered in flies, plants and mammals. miRNAs regulate gene expression by binding to the 3'-untranslated regions of mRNA and catalyze either i) cleavage of the mRNA; or 2) repression of translation. The regulation of gene expression by miRNAs is central to many biological processes such as cell development, differentiation, communication, and apoptosis (Reinhart, Slack et al. 2000; Baehrecke 2003; Brennecke, Hipfner et al. 2003; Chen, Li et al. 2004). It has been shown that miRNA are active during embryogenesis of the mouse epithelium and play a significant role in skin morphogenesis (Yi, O'Carroll et al. 2006).

Given the role of miRNA in gene expression it is clear that miRNAs will influence, if not completely specify the relative amounts of mRNA in particular cell types and thus determine a particular gene expression profile (i.e., a population of specific mRNAs) in different cell types. In addition, it is likely that the particular distribution of specific miRNAs in a cell will also be distinctive in different cell types. Thus, determination of the miRNA profile of a tissue may be used as a tool for expression profiling of the actual mRNA population in that tissue. Accordingly, miRNA levels and/or detection of miRNA mutations are useful for the purposes of disease detection, diagnosis, prognosis, or treatment-related decisions (i.e., indicate response either before or after a treatment regimen has commenced) or characterization of a particular disease in the subject.

In embodiments, nucleic acid molecules can also be isolated by lysing the cells and cellular material collected from the skin sample by any number of means well known to those skilled in the art. For example, a number of commercial products available for isolating polynucleotides, including but not limited to, RNeasy™ (Qiagen, Valencia, CA) and TriReagent™ (Molecular Research Center, Inc, Cincinnati, OH) can be used. The isolated polynucleotides can then be tested or assayed for particular nucleic acid sequences, including a polynucleotide encoding a cytokine. Methods of recovering a target nucleic acid molecule within a nucleic acid sample are well known in the art, and can include microarray analysis.

As discussed further herein, nucleic acid molecules may be analyzed in any number of ways known in the art that may assist in determining the microbiome and/or metabolome associated with an individual's skin. For example, the presence of nucleic acid molecules can be detected by DNA-DNA or DNA-RNA hybridization or amplification using probes or fragments of the specific nucleic acid molecule. Nucleic acid amplification based assays involve the use of oligonucleotides or oligomers based on the nucleic acid sequences to detect transformants containing the specific DNA or RNA.

In another embodiment, antibodies that specifically bind the expression products of the nucleic acid molecules of microbiome and/or metabolome may be used to characterize the skin lesion of the subject. The antibodies may be used with or without modification, and may be labeled by joining them, either covalently or non-covalently, with a reporter molecule.

A wide variety of labels and conjugation techniques are known by those skilled in the art and may be used in various nucleic acid and amino acid assays. Means for producing labeled hybridization or PCR probes for detecting sequences include oligolabeling, nick translation, end-labeling or PCR amplification using a labeled nucleotide. Alternatively, the nucleic acid molecules, or any fragments thereof, may be cloned into a vector for the production of an mRNA probe. Such vectors are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

PCR systems usually use two amplification primers and an additional amplicon-specific, fluorogenic hybridization probe that specifically binds to a site within the amplicon. The probe can include one or more fluorescence label moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated. In situ PCR may be utilized for the direct localization and visualization of target nucleic acid molecules and may be further useful in correlating expression with histopathological finding.

Means for producing specific hybridization probes for nucleic acid molecules of the invention include the cloning of the nucleic acid sequences into vectors for the production of mRNA probes. Such vectors are commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like

*P. acnes* is a commensal, non-sporulating bacilliform (rod-shaped), gram-positive bacterium found in a variety of locations on the human body including the skin, mouth, urinary tract and areas of the large intestine. *P. acnes* can consume skin oil and produce byproducts such as short-chain fatty acids and propionic acid, which are known to help maintain a healthy skin barrier. *Propionibacteria* such as *P. acnes* also produce bacteriocins and bacteriocin-like compounds (e.g., propionicin PiG-1, jenseniin G, propionicins SM1, SM2 T1, and acnecin), which are inhibitory toward undesirable lactic acid-producing bacteria, gram-negative bacteria, yeasts, and molds. In some embodiments, a subject having skin identified as having *P. acnes* may be treated with a personal care product designed to inhibit growth and proliferation of *P. acnes*.

In some embodiments, an individual's skin profile is translated into a personalized SkinIQ™ index, which is an overall snapshot of skin health, by capturing both the diversity of skin flora and its eminence to assist in formulating a personal care product. The main factor contributing to eminence is probiotic balance, the ratio of mutualistic and commensal microorganisms to (opportunistic) pathogens. However eminence could also comprise other factors that could positively impact the health of skin. These factors could include presence of key biosynthetic microbial genes, gene products or proteins responsible for the promotion or maintenance of healthy host skin. All these factors will contribute to the collective health of skin by, but not limited to, the reduction of skin inflammation, the reduction of the relative amounts of pathogens, and the biosynthesis of pro-vitamins, antimicrobial peptides, vitamins and fatty acids. The combination of diversity and eminence, represented by SkinIQ™ index, can also be a predictive measure of skin health. For example, a preponderance of a certain subspecies of *Propionibacterium acnes* may be strongly associated with risk of acne breakout. Similarly, SkinIQ™ may be predictive of flare ups of other skin conditions including, but not limited to, eczema, psoriasis, atopic dermatitis and rosacea.

The SkinIQ™ index is defined under Skin Health Measurement System that contrasts any individual profile to the "consensus healthy profile" from a database of skin profiles (microbiomes and/or metabolomes) and places every profile within the healthy population context. The consensus healthy profile is defined separately for each bacterial species. The data from the healthy population is used to define the range where any given bacterial species is expected to be found within healthy individuals. All these ranges define a reference for future comparisons. The Skin Health Measurement System™ further serves as a powerful discovery tool that can be used to mine a rich data set for novel microbes that can be utilized in skin care formulations to positively impact different skin conditions including, but not limited to acne, atopic dermatitis, psoriasis and eczema. Also it can be used to mine higher-level interactions between different bacterial species, with potential therapeutic implications.

As such, the invention contemplates generating a reference database containing a number of reference projected profiles created from skin samples of subjects with known states, such as normal or healthy skin, as well as various skin disease states. The individuals profile may be compared with the reference database containing the reference profiles. If the profile of the subject matches best with the profile of a particular disease state in the database, the subject is diagnosed as having such disease state. Various computer systems and software can be utilized for implementing the analytical methods of this invention and are apparent to one of skill in the art. Exemplary software programs include, but are not limited to, Cluster & TreeView (Stanford, URLs: rana.lbl.gov or microarray.org), GeneCluster (MIT/Whitehead Institute, URL: MPR/GeneCluster/GeneCluster.html), Array Explorer (SpotFire Inc, URL: spotfire.com/products/ scicomp.asp#SAE) and GeneSpring (Silicon Genetics Inc, URL: sigenetics.com/Products/GeneSpring/index.html) (for computer systems and software, see also U.S. Pat. No. 6,203,987, incorporated herein by reference).

In some embodiments, the invention provides a method of characterizing skin and/or subcutaneous tissue comprising collecting a sample from a subject containing skin or subcutaneous tissue flora. Skin and subcutaneous tissue flora of healthy individuals can be collected using swiping, scraping, swabbing, using tape strips or any other effective microbial collection method. The harvested sample can be profiled on a NGS, Sanger-sequencing, mass-spectrometry, quantitative PCR, immunofluorescence, in situ hybridization, or microbial staining based platform. For sequencing-based platforms, this can be done either using a whole-genome sequencing approach, or via targeted applications, a prominent example of which is 16S rDNA sequencing. All the above-mentioned identification methods can be implemented on samples directly collected from individuals without any proliferation step. This way, minimal bias is introduced toward identification of a mixture of culturable and unculturable microorganisms. A proprietary analysis algorithm can be used to identify species composition of each individual. A consensus healthy profile may be constructed from the healthy cohort. The healthy profile may be updated real time as more samples are collected over time. The healthy profile will serve as the reference for comparing all individual samples, i.e. profiles. Examples of identified bacteria belong to any phylum, including Actinobacteria, Firmicutes, Proteobacteria, Bacteroidetes. It will typically include common species such as *Propionibacteria, Staphylococci, Corynebacteria*, and *Acenitobacteria* species.

In some embodiments, the invention provides a platform or method for characterizing skin and subcutaneous tissue microbial flora of individuals with skin conditions. Skin and subcutaneous tissue flora of individuals with skin conditions that are considered to be suboptimal can be collected using swiping, swabbing, tape strips or any other effective microbial collection method. Collected microbial sample can be profiled on a NGS, Sanger-sequencing, mass-spectrometry, quantitative PCR, immunofluorescence, in situ hybridization, or microbial staining based platform. For the sequencing based platforms, this can be done either using a whole-genome sequencing approach, or via targeted applications, a prominent example of which is 16S rDNA sequencing. All the identification methods can be implemented on samples directly collected from individuals without any proliferation step. This way, minimal bias is introduced toward identification of a mixture of culturable and unculturable microorganisms. A personal skin and subcutaneous tissue flora profile can be generated for each individual. Individuals, based on their phenotypic characteristics, can be placed under specific skin condition categories as well. Such clustering effort will help to identify biological significant patterns which are characteristic of each cohort. The microbial composition of the affected cohort is distinct from the healthy profile. Microbial species which are associated with any given skin condition can be used as early diagnostic markers for individuals who have not developed a visual skin condition but may be prone to that. Examples of identified bacteria belong to any phylum, including Actinobacteria, Firmicutes, Proteobacteria, Bacteroidetes. It will typically include common species, such as *Propionibacteria, Staphylococci, Corynebacteria*, and *Acenitobacteria* species. Damaged skin can impact the composition of bacterial flora or can cause nonpathogenic bacteria to become pathogenic.

In some embodiments, the invention provides a platform or method for characterizing a consensus healthy skin and subcutaneous tissue metabolite profile. The metabolome associated with skin and subcutaneous tissue flora can also be profiled either by a mass-spectrometry based system or using genomics-based metabolome modeling and flux-balance analysis. Extraction can be done on samples collected by using swiping, swabbing, tape strips or any other effective microbial collection method. Alternatively, those metabolites and biochemical, specifically the extracellular ones, can be directly isolated from any individual without going through any cell harvesting. Characterization can be done on the whole metabolome or only be focused on a subset of metabolites, which are known or may be shown to be of significance in a particular disease pathology. All the above-mentioned identification methods can be implemented on samples directly collected from individuals without any proliferation step. This way, minimal bias is introduced in the population composition. A proprietary analysis algorithm may be used to identify metabolite composition of each individual's skin flora. A consensus healthy profile may be constructed from the healthy cohort. The healthy profile may be updated real time as more samples are collected over time. The healthy profile will serve as the reference for comparing all individual samples, i.e. profiles.

In some embodiments, the invention provides a platform or method for characterizing skin and subcutaneous tissue microbial flora of individuals with skin conditions. Metabolite composition of skin and subcutaneous tissue flora of individuals with skin conditions that are considered to be suboptimal can be profiled either by a mass-spectrometry based system or using genomics-based metabolome modeling and flux-balance analysis. Extraction can be done on samples collected by using swiping, swabbing, tape strips or any other effective microbial collection method. Alternatively, those metabolites and biochemical, specifically the extracellular ones, can be directly isolated from any individual without going through any cell harvesting. Characterization can be done on the whole metabolome or only be focused on a subset of metabolites, which are known or may be shown to be of significance. All the above-mentioned identification methods can be implemented on samples directly collected from individuals without any proliferation step. This way, minimal bias is introduced in the population composition. A personal profile can be generated for each individual that reflects the metabolite composition of the skin and subcutaneous tissue flora. Individuals, based on their phenotypic characteristics, can be placed under specific skin condition categories as well. Such clustering effort will help to identify biological significant patterns that are characteristic of each cohort. The metabolite composition of the affected cohort is distinct from the healthy profile. Metabolites which are associated with any given skin condition can be used as early diagnostic markers for individuals who have not developed a visual skin condition but may be prone to that.

Figure 4:
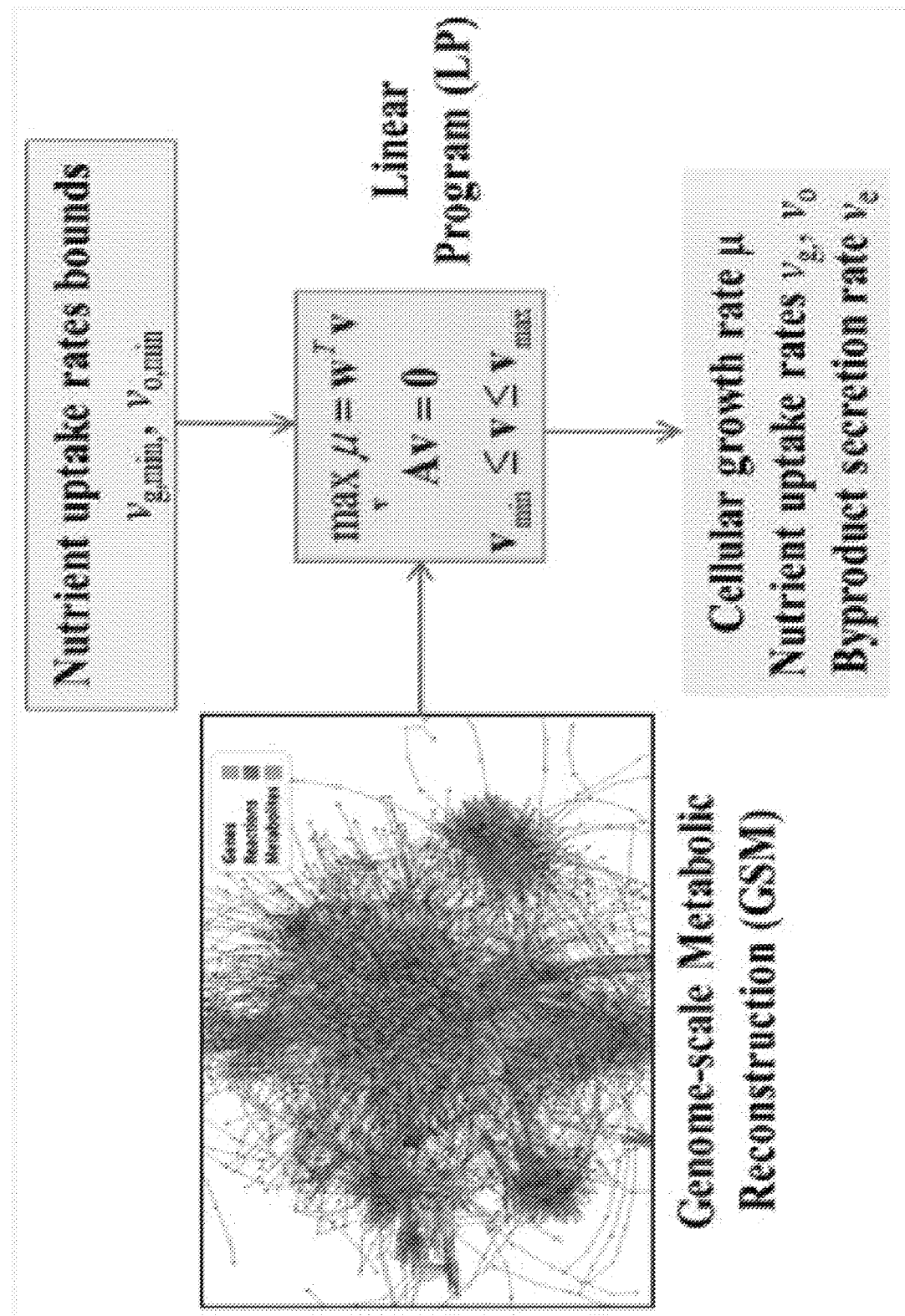
FIG. 4 shows a schematic representation of an algorithm for modeling a Genome-Scale Metabolic reconstruction or GSM as used in embodiments of the systems and methods described herein

FIG. 4 shows a schematic representation of an algorithm for modeling a Genome-Scale Metabolic reconstruction or GSM as used in embodiments of the systems and methods described herein. In some embodiments, a machine learning algorithm receives data extracted from samples comprising the microbiome and metabolome data associated with a particular sample such as a skin or hair sample. A machine learning algorithm is first trained to generate a reference database comprising threshold values for various micro-organisms and micro-organism metabolites associated with samples taken from known disease free and/or disease having individuals. The machine learning algorithm models this reference data with respect to such factors as, for example, nutrient uptake rate, cellular growth rate, and byproduct secretion rate. The machine learning algorithm receives new sample data comprising microbiome and/or metabolome data and compares new sample data against the threshold values to determine a characterization of the sample. Table 1 below shows exemplary data used to train an embodiment of the machine learning algorithm with respect to microbiomes and metabolomes of healthy individuals from the skin and/or hair samples taken from these individuals.

TABLE 1

| | |
|---|---|
| FORMULA: | C20H21N7O7 |
| BioCyc: | META: 10-FORMYL-THF |
| SEED Compound: | cpd00201 |
| UniPathway Compound: | UPC00234 |
| KEGG Compound: | C00234 |
| BioPath Molecule: | 10-Formyl-5,6,7,8-tetrahydrofolate |
| MetaNetX (MNX) Chemical: | MNXM237 |
| Reactome: | 419151; 5389850 |
| Human Metabolome Database: | HMDB00972 |
| FORMULA: | C10H12N5O10P2 |
| BioCyc: | META: ADP; META: ADP-GROUP |
| SEED Compound: | cpd00008 |
| UniPathway Compound: | UPC00008 |
| KEGG Compound: | C00008; G11113 |
| BioPath Molecule: | Adenosine-5-prime-diphosphate |
| MetaNetX (MNX) Chemical: | MNXM7 |
| Reactome: | 113581; 113582; 114565; 211606; 29370; 5632457 |
| Human Metabolome Database: | HMDB01341 |
| FORMULA: | C10H12N5O13P3 |
| BioCyc: | META: ATP |
| SEED Compound: | cpd00002 |
| UniPathway Compound: | UPC00002 |
| KEGG Compound: | C00002; D08646 |
| BioPath Molecule: | Adenosine-5-prime-triphosphate |
| MetaNetX (MNX) Chemical: | MNXM3 |
| Reactome: | 211579; 389573 |
| Human Metabolome Database: | HMDB00538 |

Figure 5:
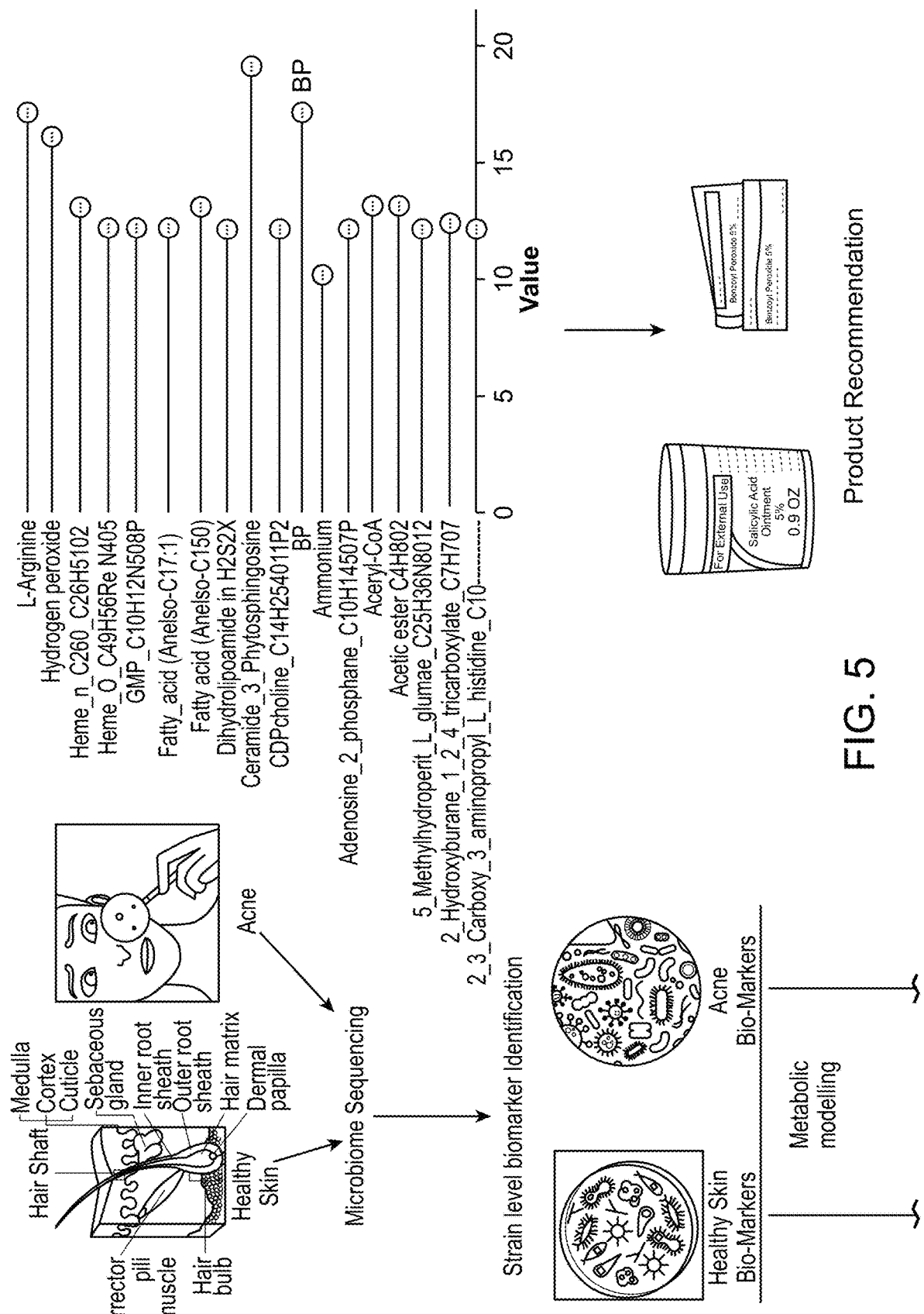
FIG. 5 shows a schematic representation of a method for classifying a sample taken from an individual and providing a custom therapy to the individual.
Figure 5:
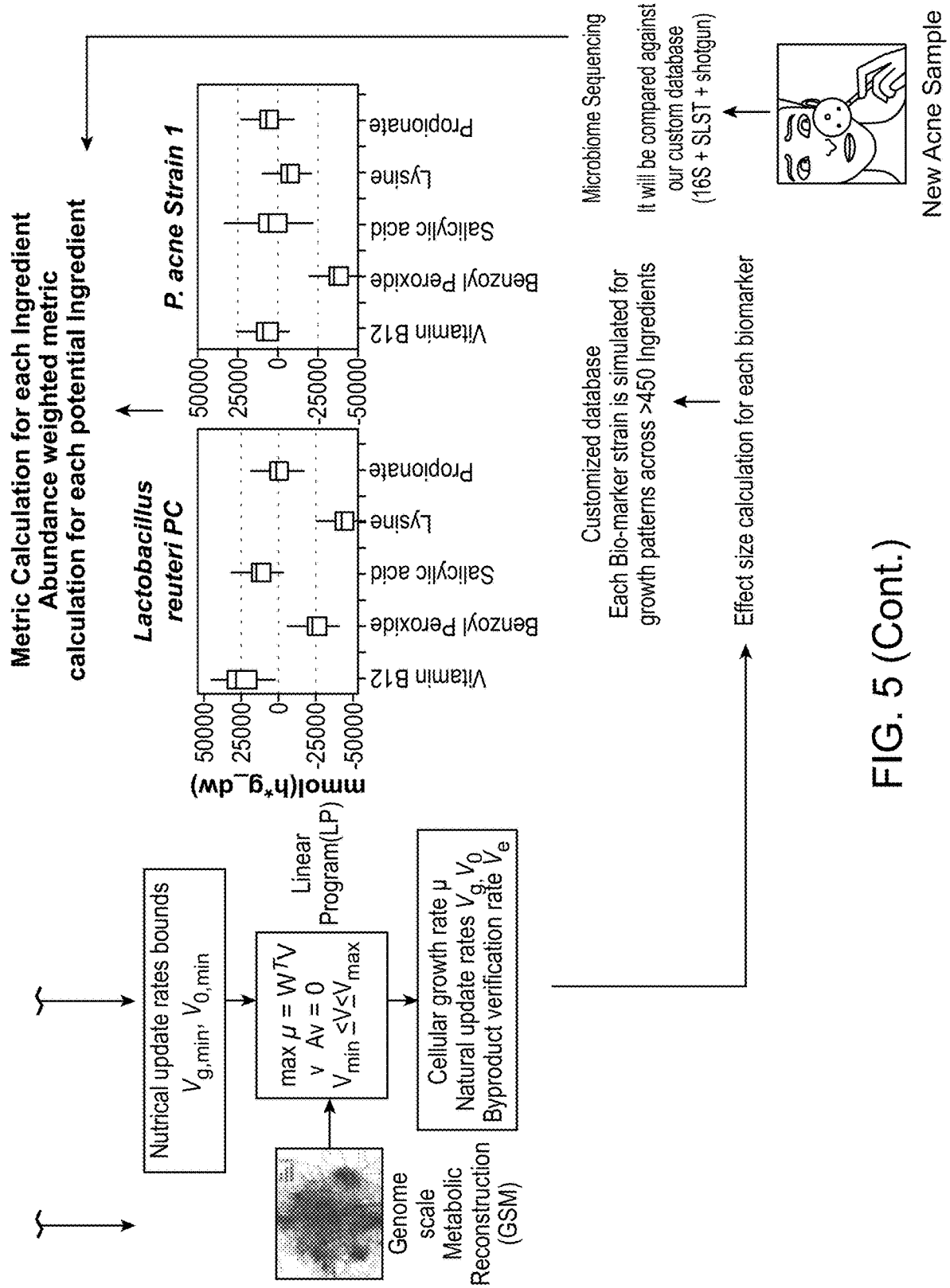

FIG. 5 shows a schematic representation of a method for classifying a sample taken from an individual and providing a custom therapy to the individual. In a first step a sample, such as a skin or hair sample, is sequenced as described herein. In a second step, certain biomarkers are identified including, for example, biomarkers that indicate healthy skin and those that indicate the presence of acne. In a third step, a metabolome is determined and then in a fourth step, metabolic modeling is performed using, for example, the algorithm of FIG. 4. In a fifth step, the effective size or relative representation of each biomarker is determined. In a sixth step, each biomarker strain is modeled in a manner that simulates the growth of each biomarker in the presence of various ingredients and potential ingredients of a custom therapy are identified based on the results of the model and objectives for either stimulating or inhibiting the growth of certain biomarkers. In a seventh step, an abundance weighted metric calculation for each potential ingredient is determined. In an eighth step, a custom therapy is recommended (or generated) based on the results of steps one through seven. In an optional ninth step, a new sample is analyzed using one or more of steps one through nine. It should be understood that one or more of these steps are omitted in certain embodiments of the method and in certain embodiments of the method one or more steps of the method are performed in a different order.

Accordingly, in one aspect, the invention provides a method of characterizing a microbiome of skin or subcutaneous tissue of a subject. The method includes: a) obtaining a sample comprising a plurality of microorganisms from the skin or subcutaneous tissue of the subject; and b) analyzing and classifying the plurality of microorganisms to characterize the microbiome of the subject, thereby characterizing the microbiome of the subject. In some embodiments, the method further includes comparing the microbiome of the subject to a reference microbiome or generating a microbiome profile of the subject, or identifying a disease or disorder which the subject has, or is at risk of developing, or providing a personalized treatment regime to the subject. In various embodiments, the reference microbiome is classified as having a healthy profile and a similarity between the microbiome of the subject and the reference microbiome identifies the microbiome of the subject as having a healthy profile. Alternatively, the reference microbiome is classified as having, or at risk of having a disease or disorder and a similarity between the microbiome of the subject and the reference microbiome identifies the microbiome of the subject as having as having, or at risk of having the disease or disorder.

Systems and Methods for Providing Customized Treatments

Traditional treatments of dermatological conditions include use of antibiotics and/or anti-inflammatories. An unwanted side-effect of antibiotics (and especially antibiotics that have an overly broad spectrum) tend to alter an individual's microbiome in ways that are more detrimental than beneficial. That is, antibiotics are best suited for treating bacterial infections whereas many dermatologic disease processes are associated with or caused by bacterial overgrowth which creates bacterial/micro-organism imbalance. Infection differs from micro-organism imbalance in a number of ways. Fundamentally, infection is treated by eradication of the infectious micro-organism whereas micro-organism imbalance is typically best treated by adjusting or re-equilibrating the balance of micro-organism in areas of skin where the imbalance exists, and not by eradication of the micro-organism in the affected area. As such, antibiotic treatment of individuals who suffer certain dermatologic disorders tends to eradicate bacteria including normal components of the microbiome, rather than re-equilibrating the micro-organisms of the microbiome, and as such, antibiotic treatment tends to cause certain adverse effects and imbalances. Anti-inflammatory agents, and in particular steroid base anti-inflammatory agents, tend to attenuate the body's immune response and thus attenuating the epidermal cell's response to pathogens and as such tend to have certain adverse effects. Along the same lines, traditional antibiotic and anti-inflammatory treatments tend not to address the underlying pathophysiology of the certain dermatologic disorders, because, for example, these traditional therapies tend to be overly broad in their mode of action which results in many cases in harmful imbalances in the microbiome and immune system of the individual being treated.

Described herein are customized skin care and personal care products for human and animal use and, more particularly, but not by way of limitation, the development of personal care products that are based on the initial evaluation of the flora inhabiting the skin and subcutaneous tissue. Described herein are systems and methods for analyzing the skin and subcutaneous tissue flora and its associated metabolome, comparing the resulting profile of the skin and subcutaneous tissue flora and metabolome to a healthy profile, represented as a quantity and diversity of flora that falls within a range determined from a set of healthy skin types, and then customizing skin care and personal care products that will augment the flora residing on a test subject's skin and subcutaneous tissue and its associated metabolome or replicate a healthy flora profile on to that of a test subject.

Individualized skin test result are used as the basis for development of individualized skin care and personal care products which are customized to either maintain a healthy skin microbiome and metabolome or shift a profile towards a healthy equilibrium or state by adding one or more commensal and/or mutualistic organisms and/or substrates that favor the growth of commensal and mutualistic organisms on the skin.

The exact composition of the skin care product blend may be determined after comparing the resulting profile of any individual's skin and subcutaneous tissue flora and metabolome to a healthy profile and then customizing skin care and personal care products that best shift the subject's skin and subcutaneous tissue flora and metabolome toward a healthy profile. The optimal flora and substrates and metabolomes would also synergize with host's immune system and contribute toward a healthy skin from that perspective.

Furthermore, the composition of subject's flora and metabolome may be compared to previously complied database of different skin conditions to see whether he or she is prone to develop any of those skin conditions in future. Based on the customized or personalized test results, a customized or personalized skin care or personal care blend may be formulated for that individual by blending a mixture of commensal and mutualistic microorganisms or their relevant metabolites that are depleted in that individual's flora or metabolome with or without the necessary substrates and nutrients that favor proliferation of commensal and mutualistic organisms. This customized or personalized skin care or personal care product is specifically created in a way to establish an optimal profile by either maintaining a healthy microbiome or shifting the suboptimal profile towards a healthy equilibrium. Also the synergies between the optimal microbial flora and its associated metabolome and host's immune system will further contribute to skin health and wellness.

Skin care products or personal care products suitable for use with the systems and methods described herein, in some embodiments, include skin care products and include, but are not limited to, cleansing products, shampoo, conditioner, toners or creams, topical ointments and gels, as well as localized (e.g. under eye) gel, all of which may be formulated to contain ingredients specifically designed to shift microbial population to a healthy profile with or without a commensal or mutualistic organism or mixture of commensal or mutualistic organisms in either an active or dormant state. Such skin care products may further include therapeutic agents, vitamins, antioxidants, minerals, skin toning agents, polymers, excipients, surfactants, probiotics or fraction thereof, microorganism or product from the culture thereof, such a bacteria, fungi and the like, either living, dormant or inactive.

In some embodiments, the platform or method described herein may be provided as a test for profiling the skin flora of any individual, either healthy or with a skin condition and also their associated metabolome. Such test would be sensitive to characterize the dominant skin flora and metabolites of any individual. A customized or personalized evaluation of any individual's flora may be conducted and identified skin and subcutaneous tissue flora and metabolites may be compared to healthy and also affected skin profiles. A customized or personalized report may be generated which will specify species composition of the individual's skin and subcutaneous tissue flora and also its associated metabolites. Such report will enlist the beneficial and commensal species that are depleted or over-represented in each individual. It will also include the list of beneficial or undesired metabolites that are either depleted or over-represented in each individual. This may be used for formulation of the customized or personalized skin care or personal care product. Alternatively, the test can be administered to assess the performance of other skin care and personal care products, therapies, or evaluate any disruption of the normal skin flora or metabolites. The test can be performed before, during, and after any skin treatment in order to monitor the efficacy of that treatment regimen on skin flora or its associated metabolites. The test can also be used for early diagnostic of skin conditions that are associated with a signature microbial profile or their accompanying metabolites. The sensitivity of the test allows early diagnostic of such skin conditions before their phenotypic outbreak. In an aspect, the invention provides a method for generating, or a customized or personalized skin care or personal care product formulated for a particular individual. The customized or personalized product contains one or more beneficial or commensal microorganisms or a set of chemicals and metabolites which may be depleted in any given individual. Regular administration of such skin care products and personal care products should shift the suboptimal profile towards a healthy equilibrium. Skin care product may be applied after cleansing the existing flora with a proprietary lotion that will enhance the efficacy of colonization of skin care product microorganisms or its constituent metabolites. Any customized or personalized skin care or personal care product can contain one or more microorganisms, culturable or unculturable. The customized or personalized product can alternatively be a substrate and nutrients that favor the establishment or proliferation of mutualistic or commensal organisms and/or suppression of pathogenic organisms. Those chemicals and metabolites are either synthesized in vitro or purified from a microorganism.

Figure 6:
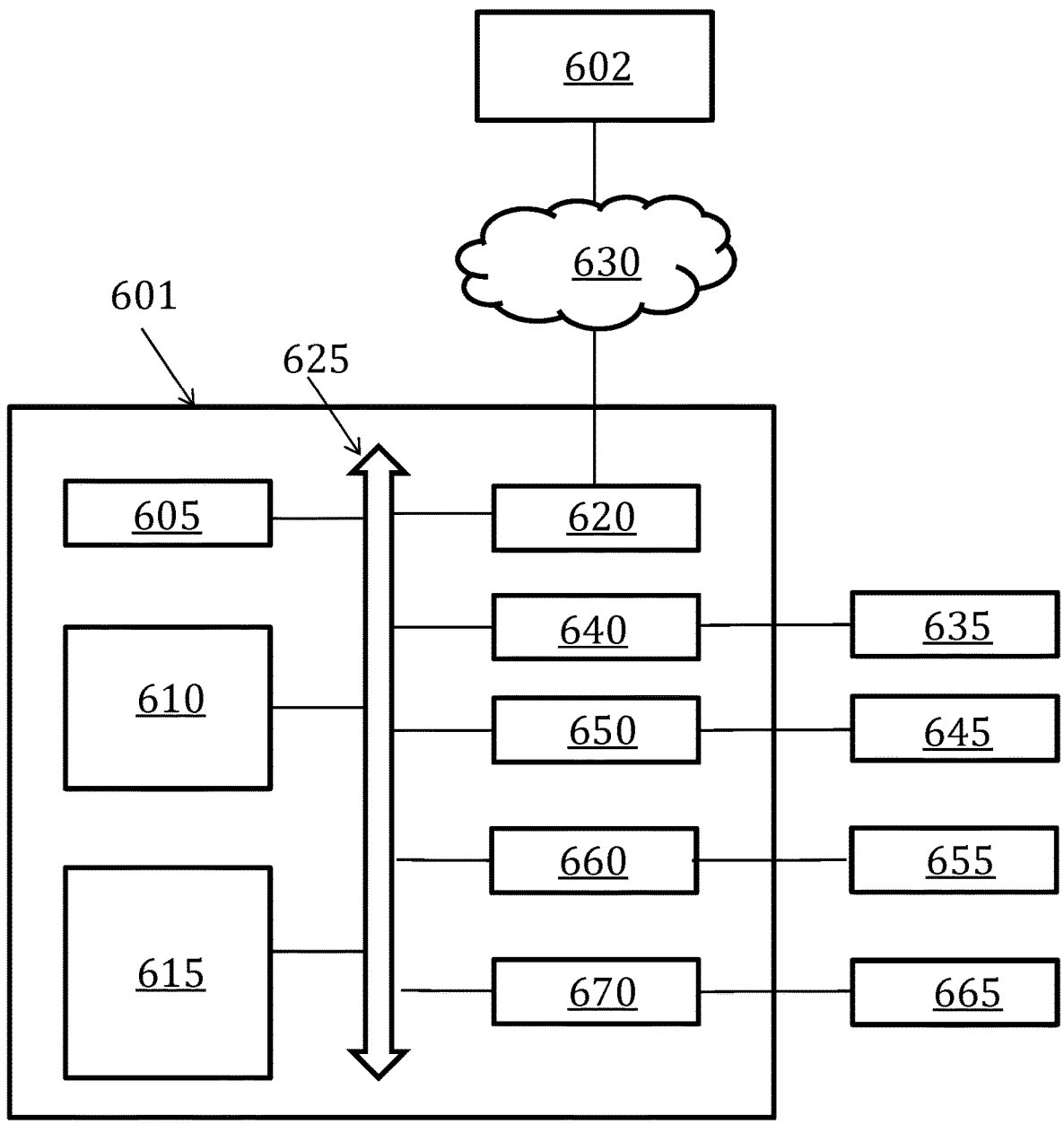
FIG. 6 shows an exemplary embodiment of a system as described herein

FIG. 6 shows an exemplary embodiment of a system as described herein. In some embodiments, a system comprises a digital processing device 601. The digital processing device 601 includes a software application configured to characterize a sample taken from an individual and in some embodiments further determine a custom therapy for an individual. The digital processing device 601 may include a central processing unit (CPU, also "processor" and "computer processor" herein) 605, which can be a single core or multi-core processor, or a plurality of processors for parallel processing. The digital processing device 601 also includes either memory or a memory location 610 (e.g., random-access memory, read-only memory, flash memory), electronic storage unit 615 (e.g., hard disk), communication interface 619 (e.g., network adapter, network interface) for communicating with one or more other systems, and peripheral devices, such as cache. The peripheral devices can include storage device(s) or storage medium 665 which communicate with the rest of the device via a storage interface 670. The memory 610, storage unit 615, interface 619 and peripheral devices are configured to communicate with the CPU 605 through a communication bus 1925, such as a motherboard. The digital processing device 601 can be operatively coupled to a computer network ("network") 630 with the aid of the communication interface 619. The network 630 can comprise the Internet. The network 630 can be a telecommunication and/or data network.

The digital processing device 601 includes input device(s) 645 to receive information from a user, the input device(s) in communication with other elements of the device via an input interface 650. The digital processing device 601 can include output device(s) 655 that communicates to other elements of the device via an output interface 660.

The CPU 605 is configured to execute machine-readable instructions embodied in a software application or module. The instructions may be stored in a memory location, such as the memory 610. The memory 610 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 110 can also include a basic input/output system (BIOS), including basic routines that help to transfer information between elements within the digital processing device, such as during device start-up, may be stored in the memory 610.

The storage unit 615 can be configured to store files. The storage unit 615 can also be used to store operating system, application programs, and the like. Optionally, storage unit 615 may be removably interfaced with the digital processing device (e.g., via an external port connector (not shown)) and/or via a storage unit interface. Software may reside, completely or partially, within a computer-readable storage medium within or outside of the storage unit 615. In another example, software may reside, completely or partially, within processor(s) 605.

Information and data can be displayed to a user through a display 635. The display is connected to the bus 625 via an interface 640, and transport of data between the display other elements of the device 601 can be controlled via the interface 640.

Methods as described herein can be implemented by way of machine (e.g., computer processor) executable code stored on an electronic storage location of the digital processing device 601, such as, for example, on the memory 610 or electronic storage unit 615. The machine executable or machine readable code can be provided in the form of a software application or software module. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

A remote device 602, in some embodiments, is configured to communicate with the digital processing device 601, and may comprises any mobile computing device, non-limiting examples of which include a tablet computer, laptop computer, smartphone, or smartwatch. The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Microbiome Characterization for Assessment of Body Odor

General Description

Skin swabs were collected from two cohorts of individuals: with high and low underarm body odor. Samples from each individual were collected from underarm, underarm hair follicles, and behind the neck. Swabs were processed through a microbiome profiling workflow described herein.

Concepts Covered

For underarm, the epidermal microbiome can reflect the deeper dermal microbiome associated with hair follicles with a very significant concordance.

Microbiome composition of the underarm highly impacts underarm body odor status.

*Staphylococcus* species were more abundant in low odor individuals and *Corynebacterium* and *Propionibacterium* species were more common in high odor individuals.

Comparing the functional profiles of high and low odor individuals, these functional categories are more active in high odor individuals: biosynthesis of secondary metabolites; transport and catabolism; and membrane transport regulation.

Different *P. acnes* strains have differential abundances in high versus low body odor individuals.

A predictive characterization model can be built using machine learning to classify individuals to high or low body odor based on the microbiome composition.

Results

Average Composition (Microbiome)

The average microbial compositions of the three sites were compared.

For behind the neck, the dominant bacteria was *Propionibacterium acnes*.

For underarm and hair follicles, *Staphylococcus* species were the most prevalent bacteria.

Figure 7:
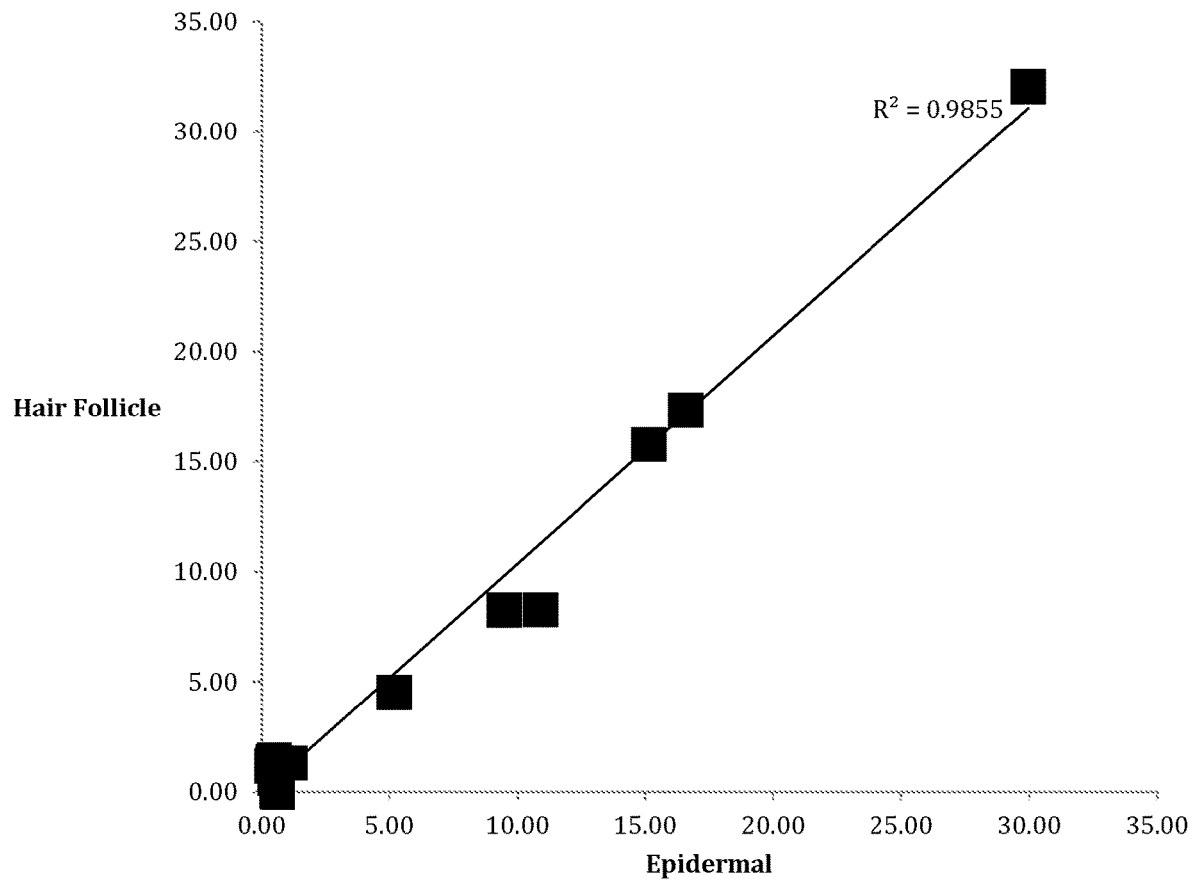
FIG. 7 shows a graph showing average microbial composition in one embodiment of the invention.

The average profile of underarm and hair follicles showed significant similarity (see FIG. 7). FIG. 7 demonstrates the correlation between microbiome composition in a skin swab collected from the underarm ("Epidermal") and microbiome composition in a skin swab collected from the underarm hair follicles ("Hair Follicle"). Each black dot corresponds to the prevalence of a prominent bacteria in the underarm epidermal microbiome (X-axis) and the underarm hair follicle (Y-axis). The dots show the average frequency of the most prominent bacteria in hair pluck versus underarm.

This similarity proves that for underarm, the epidermal microbiome can nicely reflect the deeper dermal microbiome associated with hair follicles.

Figure 8:
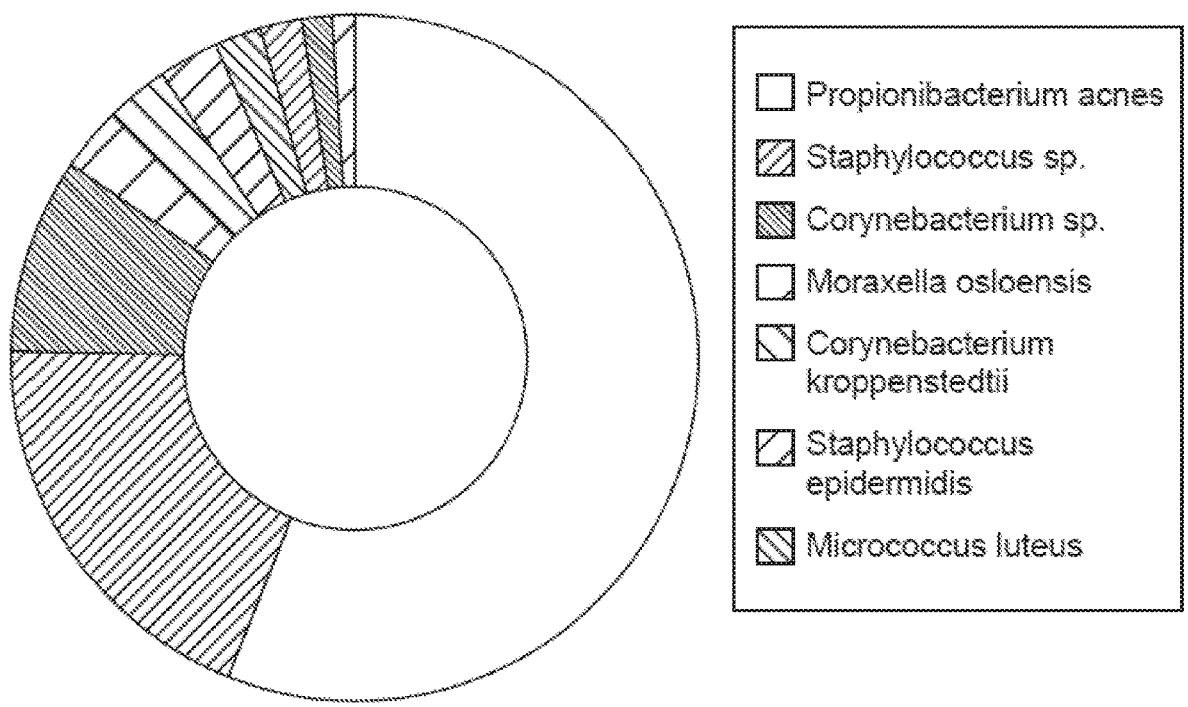
FIG. 8 shows a graph showing microbial composition in one embodiment of the invention.

FIG. 8 depicts an exemplary illustration of the average microbial composition in sample obtained from a skin swab collected from behind the neck.

Figure 9:
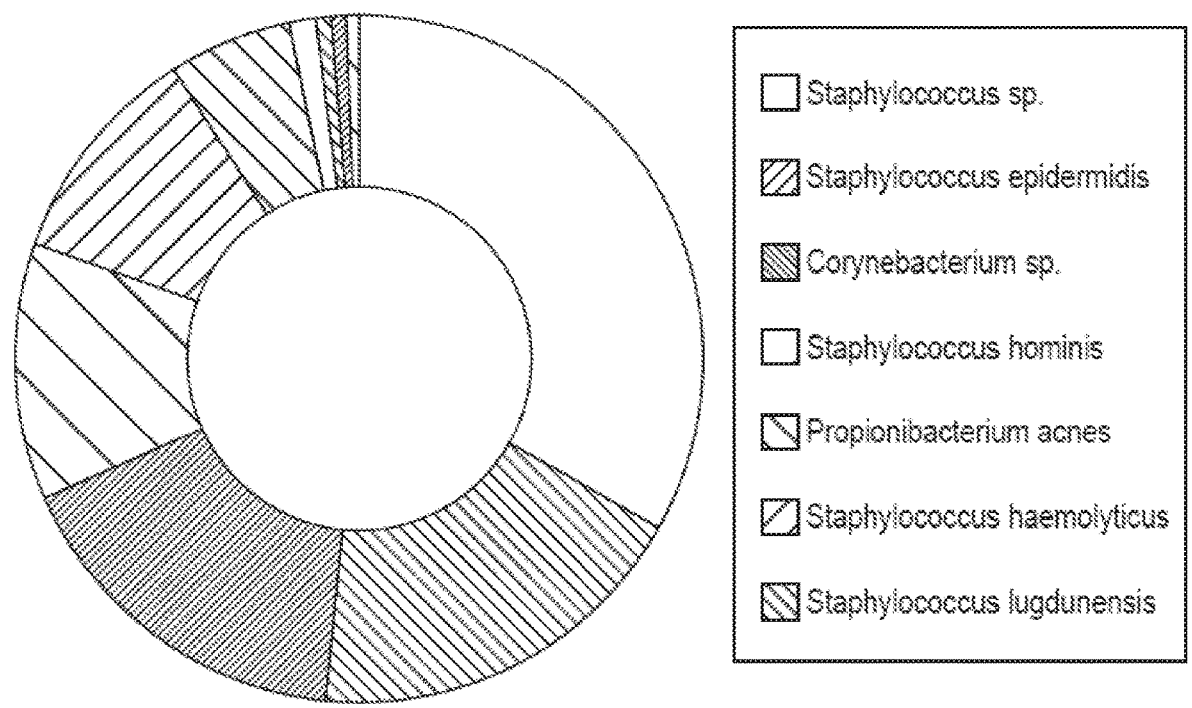
FIG. 9 shows a graph showing microbial composition in one embodiment of the invention.

FIG. 9 depicts an exemplary illustration of the average microbial composition in sample obtained from a skin swab collected from the underarm region of a subject.

Figure 10:
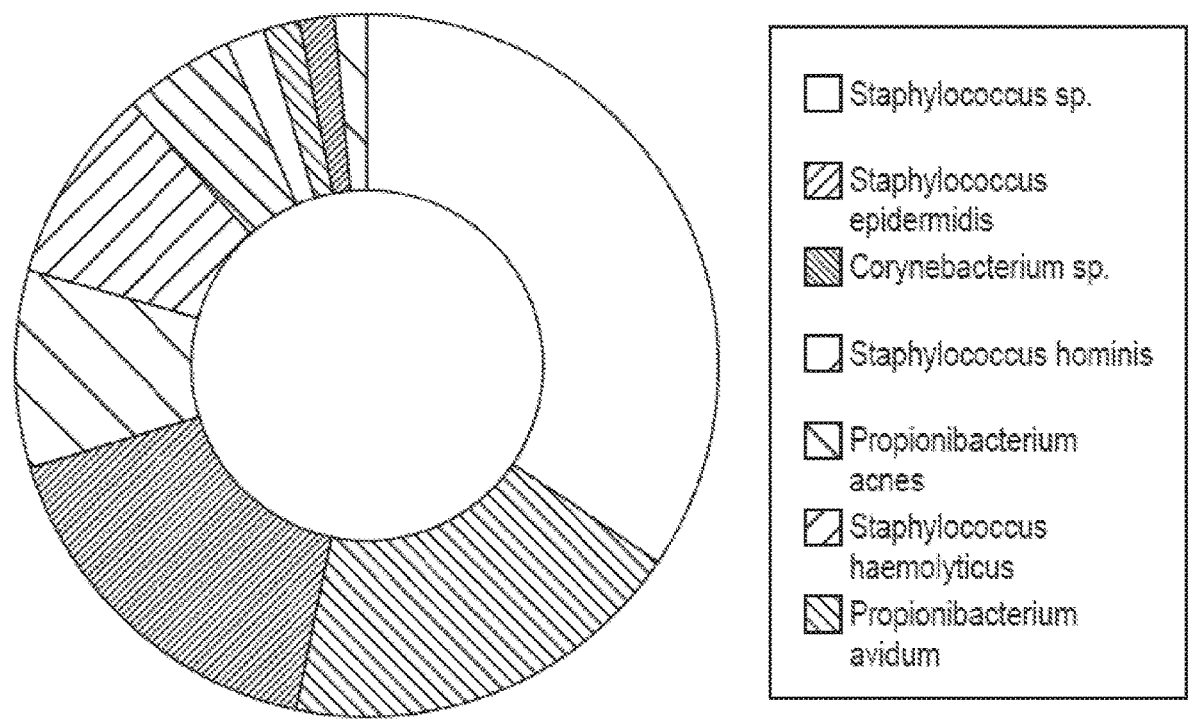
FIG. 10 shows a graph showing microbial composition in one embodiment of the invention.

FIG. 10 depicts an exemplary illustration of the average microbial composition in sample obtained from a skin swab collected from the underarm hair follicles of a subject.

Differential Composition

Differential Composition in Underarm

Microbiome composition of the underarm samples were compared between high and low odor individuals. Two group analysis was performed using Welch's t-test with Sotry's FDR correction method. Effect filter size was set on=0.2.

*Staphylococcus* species were more abundant in low odor individuals and *Corynebacterium* and *Propionibacterium* species were more common in high odor individuals.

Figure 11:
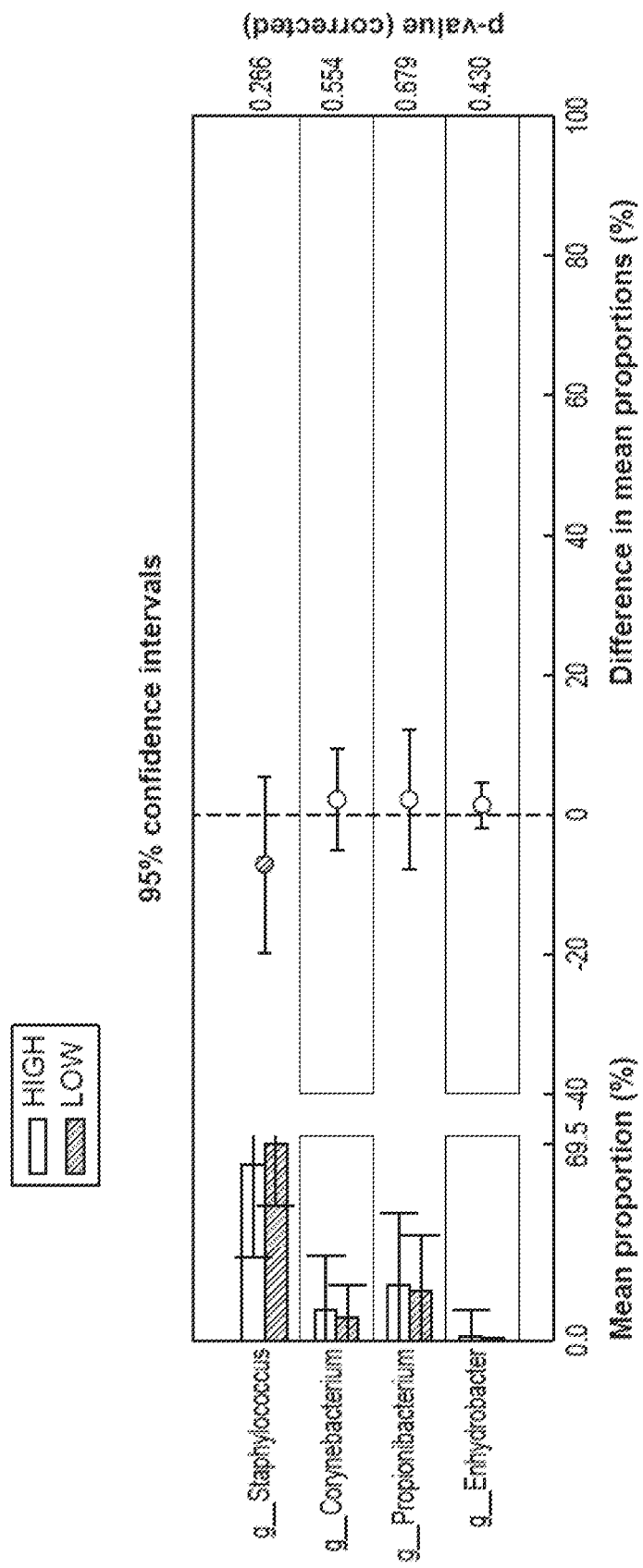
FIG. 11 shows a graph showing differential microbial composition in one embodiment of the invention.

Results are shown in FIG. 11. FIG. 11 illustrates differences in microbiome species abundance in the underarm skin swabs of high odor and low odor subjects.

The species level analysis will be carried out next to evaluate the difference.

Functional Inference

Functional Prediction, Underarm

Two group analysis was performed using Welch's t-test with Sotry's FDR correction method. Effect filter size was set on=0.2.

Comparing the functional profiles of high and low odor individuals, these functional categories are more active in high odor individuals: biosynthesis of secondary metabolites; transport and catabolism; and membrane transport regulation.

Higher activity of transport and catabolism and membrane transport regulation in high odor individuals makes sense, because the odor is believed to be caused by break-down of sweat components through bacteria which requires an active membrane activity.

Secondary metabolites like diacetyl 2,3-butanedione, isovaleric acid and propionic acid are also commonly associated with body odor.

Figure 12:
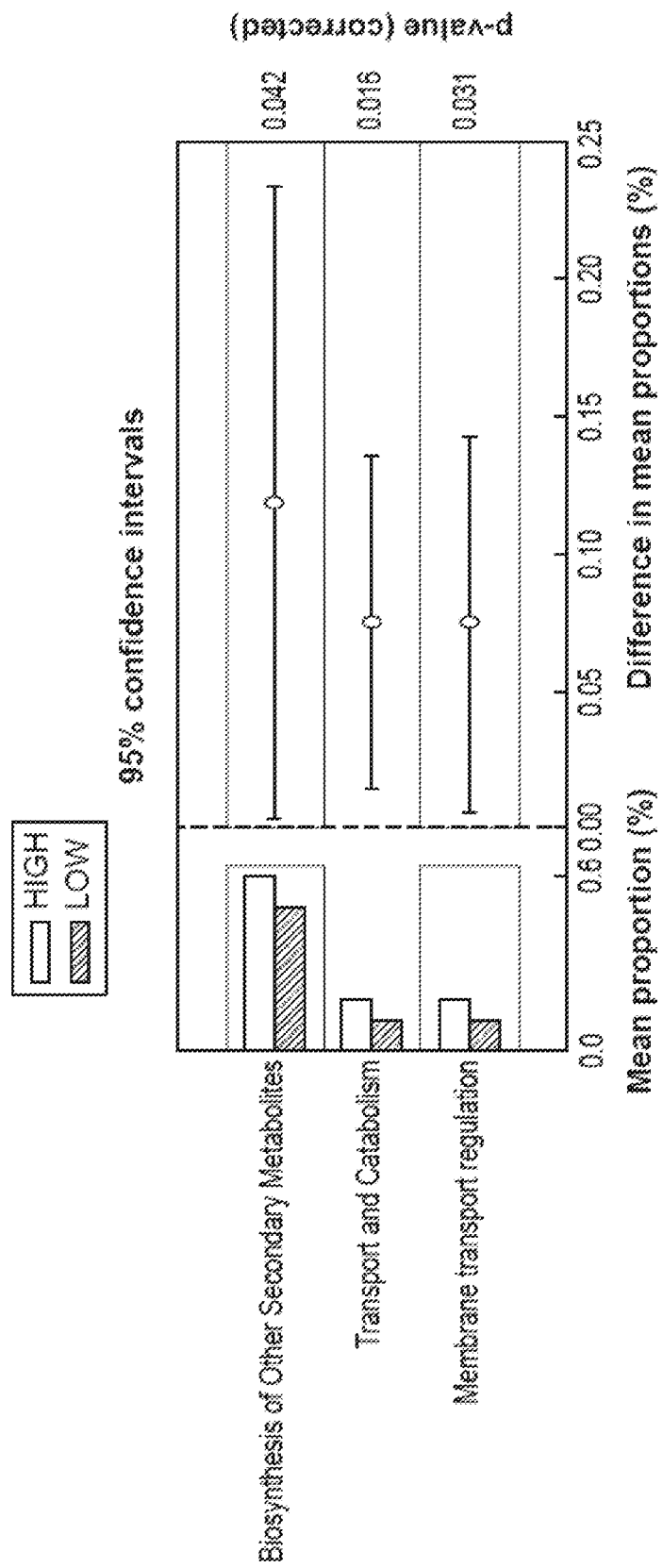
FIG. 12 shows a graph depicting experimental data in one embodiment of the invention.

Results are shown in FIG. 12. FIG. 12 classifies the microbiome composition into functional categories and shows that 'Biosynthesis of Other Secondary Metabolites'; 'Transport and Catabolism'; and 'Membrane transport regulation' are three categories elevated in the underarm region of individuals with high body odor.

Functional Prediction, Underarm, Pathway Level

Two group analysis was performed using welch's t test with Sotry's FDR correction method. Effect filter size was set on=0.2.

Porphyrin metabolism is more active in high odor individuals. Porphyrin may contribute to perifollicular inflammatory reaction through their cytotoxic effect and by stimulating expression of keratinocyte-derived IL-8.

Bacteria in high-odor individuals seems to be more metabolically active based on the comparative analysis of the TCA cycle.

Higher butanoate metabolism in high-odor individuals is noteworthy as butyrate has a strong odor.

Figure 13:
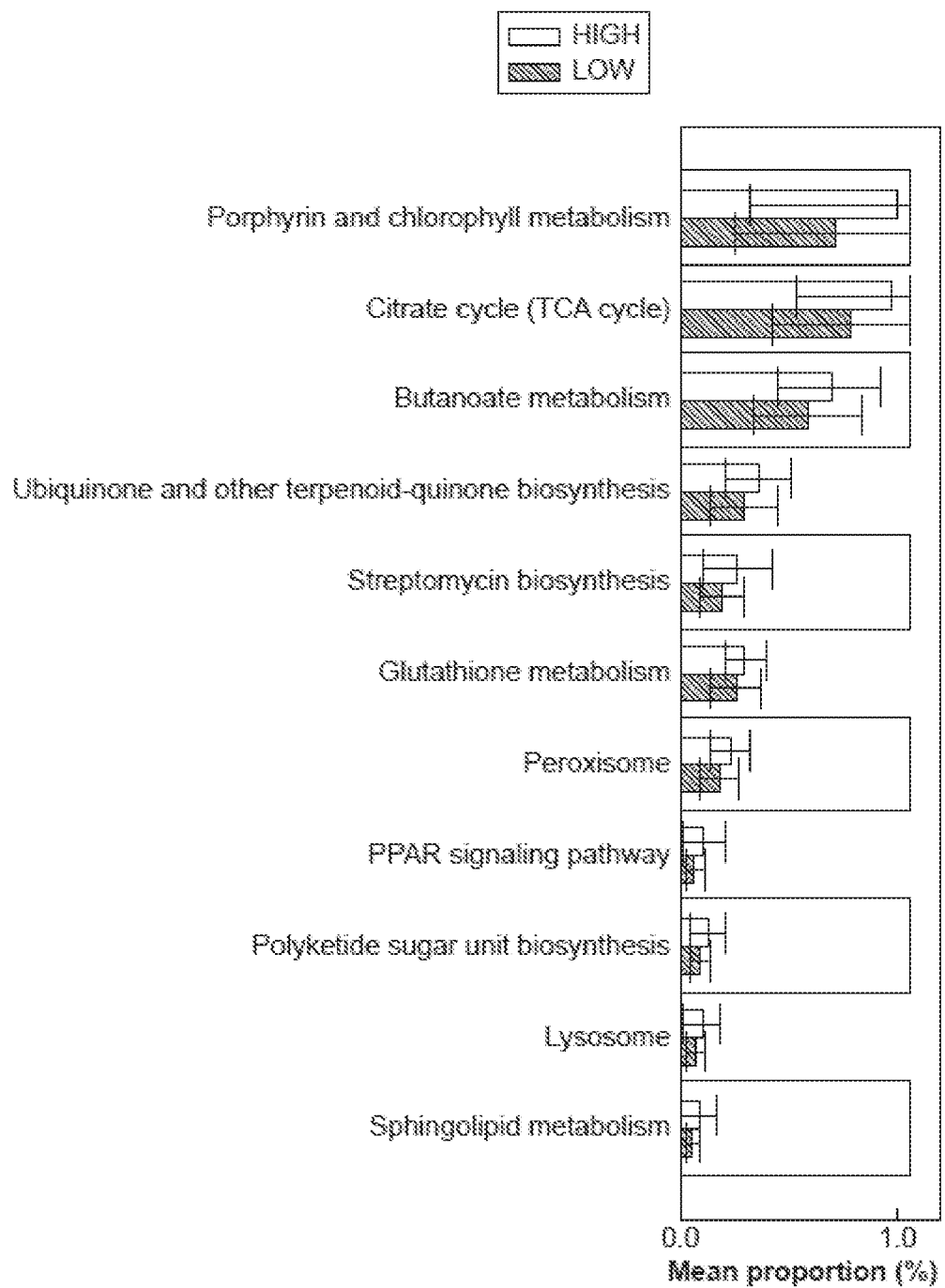
FIG. 13 shows a graph depicting experimental data in one embodiment of the invention.

Results are shown in FIG. 13. FIG. 13 expands on the characterization performed in FIG. 9 and breaks the microbiome composition into pathways. The results in FIG. 10 show that porphyrin metabolism, TCA cycle, and butanoate metabolism is more active in the underarm region of high odor individuals.

P. acnes Typing

Figure 14:
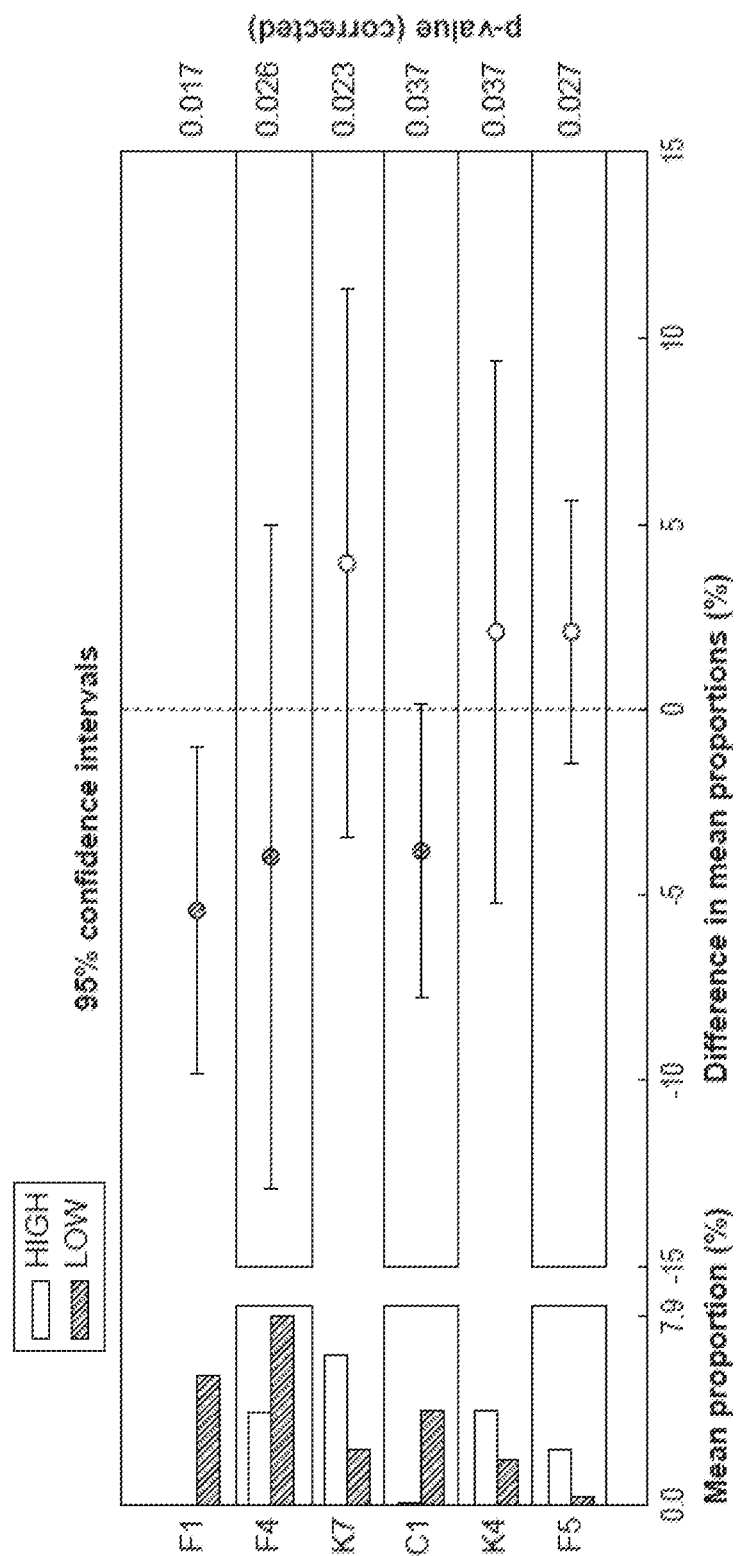
FIG. 14 shows a graph depicting differential mapping data in one embodiment of the invention.

P. acnes SLST Differential Mapping in hair plucks is shown in FIG. 14. FIG. 14 depicts single locus single trait (SLST) differential mapping and shows the prevalence of various P. acnes types in high odor and low odor subjects based on the microbiome composition analysis of the underarm hair follicle.

P. acnes F1 and C1 are almost exclusively found in low body odor individuals while F5 is found mostly in high body odor individuals.

Figure 15:
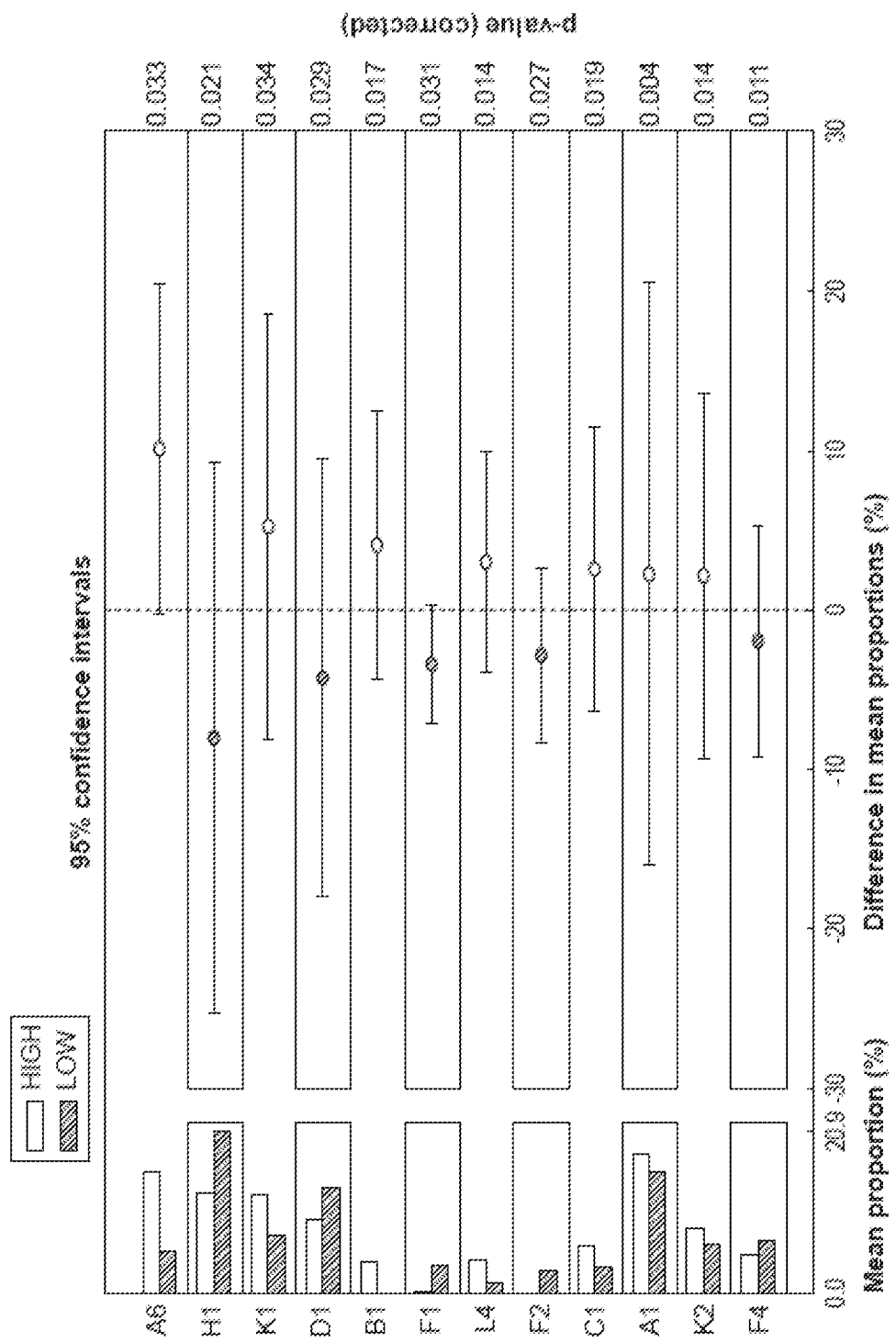
FIG. 15 shows a graph depicting differential mapping data in one embodiment of the invention.

P. acnes SLST Differential Mapping in underarm is shown in FIG. 15. FIG. 15 depicts single locus single trait (SLST) differential mapping and shows the prevalence of various P. acnes types in high odor and low odor subjects based on the microbiome composition analysis of the underarm.

In underarm, A6 & B1 is found with higher abundance in high body odor individuals while F1 was the opposite.

Body Odor Model

Data was used to build a model that can predict if an individual is high or low body odor.

The characterization model uses the odor status of low or high samples and correlates it with the OTU abundance. The created model will predict the odor status of the test set and will classify it as a "high" or "low".

Figure 16:
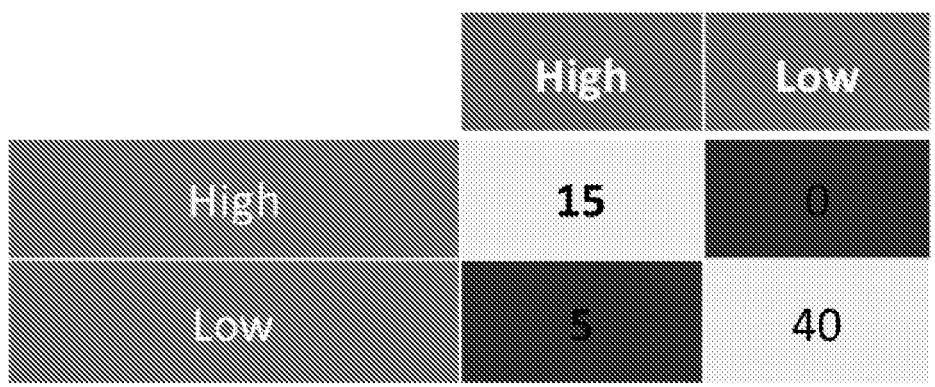
FIG. 16 shows a table presenting results relating to a generated body odor model.

As shown in FIG. 16, the model has accuracy of 55/60=0.92. FIG. 16 shows that the model accurately predicted 15 high odor individuals who were actually high odor individuals, and accurately predicted 40 low odor individuals who were actually low odor individuals.

Figure 17:
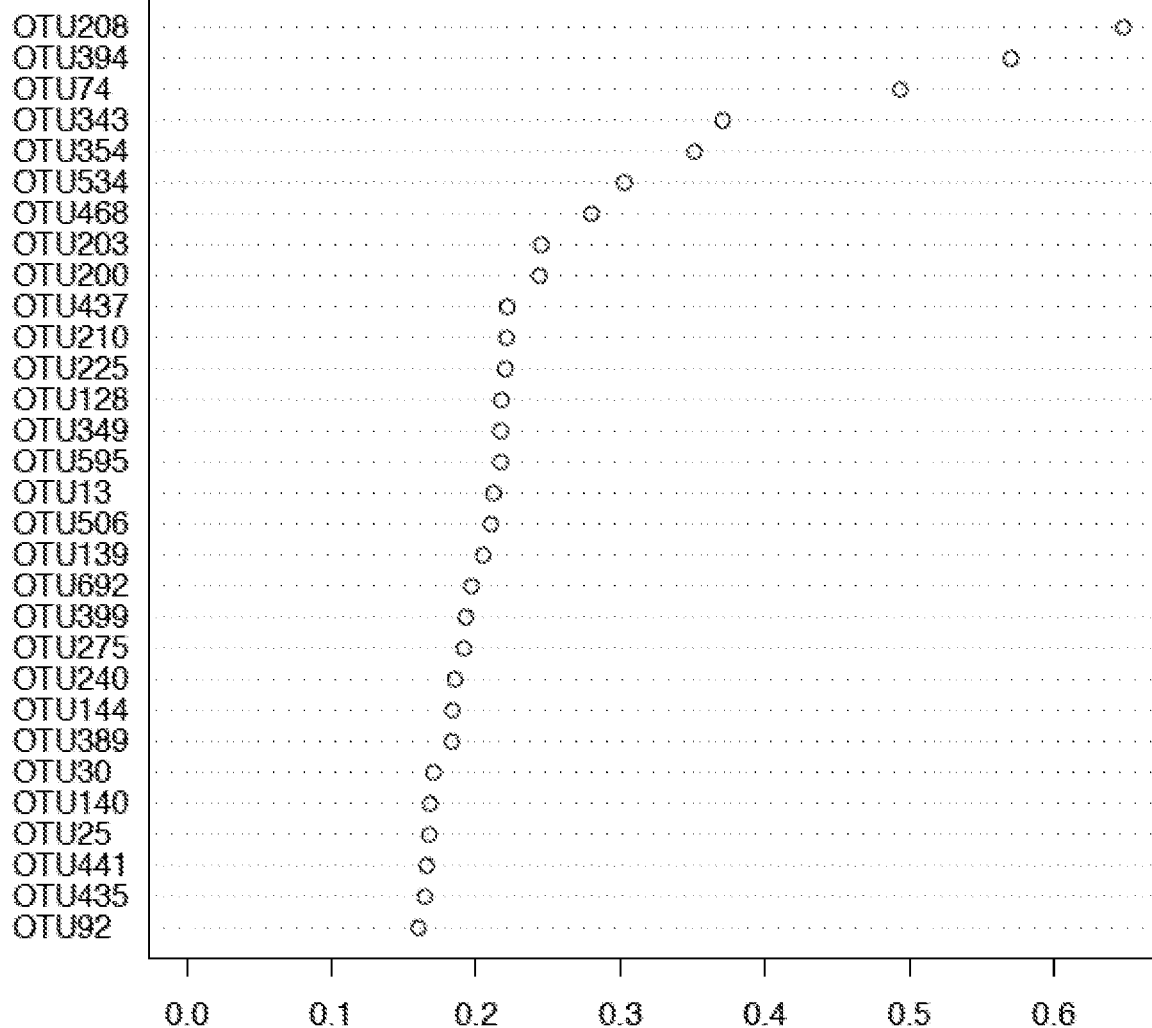
FIG. 17 shows a graph presenting results relating to a generated body odor model.

FIG. 17 shows the contribution of different Operational Taxonomic Units (OTUs) to the predictive power of the model.

Although the invention has been described with reference to the above examples, it will be understood that modifications and variations are encompassed within the spirit and scope of the invention.

What is claimed is:

1. A method for characterizing a skin disease or disorder of an individual who provides a skin microbiome, comprising:
    (a) generating a skin sequence profile comprising a set of nucleotide sequences of nucleic acids of said skin microbiome associated with a skin sample of said individual;
    (b) generating a skin metabolome profile of metabolites of said skin sample, wherein said skin metabolome profile comprises a member selected from the group consisting of a cellular growth rate associated with said skin microbiome, a nutrient uptake rate associated with said skin microbiome, and a byproduct secretion rate associated with said skin microbiome;
    (c) comparing said skin sequence profile and said skin metabolome profile to a reference skin profile thereby generating a comparison result, wherein said reference skin profile comprises a reference skin microbiome profile and a reference skin metabolome profile, wherein said reference skin profile is generated at least in part on skin microbiome data and skin metabolome data from a first population of individuals who have said skin disease or disorder or a second population of individuals who do not have said skin disease or disorder; and
    (d) generating a characterization of said skin disease or disorder of said individual based at least in part on said comparison result.

2. The method of claim 1, wherein said individual is characterized as an odoriferous individual.

3. The method of claim 1, wherein said set of nucleotide sequences is generated using whole genome sequencing, next-generation sequencing, Sanger sequencing, 16S ribosomal deoxyribonucleic acid (rDNA) sequencing, or 16S ribosomal ribonucleic acid (rRNA) sequencing.

4. The method of claim 1, wherein said skin microbiome profile comprises a bacterium selected from the group consisting of genus *Propionibacteria*, genus *Staphylococci*, and genus *Corynebacteria*.

5. The method of claim 1, wherein said skin reference profile is generated at least in part by a machine learning algorithm trained with said skin microbiome data and said skin metabolome data.

6. The method of claim 1, wherein said comparison result is generated at least in part by a machine learning algorithm trained with said skin microbiome data and said skin metabolome data from both said first population and said second population.

7. The method of claim 5, wherein said skin disease or disorder comprises acne vulgaris or body odor.

8. The method of claim 1, wherein said characterization of said skin disease or disorder of said individual comprises a determination of a presence of said skin disease or disorder and a relative degree of said presence of said skin disease or disorder.

9. The method of claim 1, wherein said comparison result, said skin sequence profile, or said skin metabolome profile is used to determine a custom treatment modality for said individual, wherein said custom treatment modality comprises an agent that promotes growth of a microorganism within said skin microbiome.

* * * * *